United States Patent
Knappe et al.

(10) Patent No.: US 8,999,309 B2
(45) Date of Patent: Apr. 7, 2015

(54) HAIR PREPARATION CONTAINING TWO COPOLYMERS

(75) Inventors: Thorsten Knappe, Schenefeld (DE); Rene Scheffler, Ellerau (DE); Rolf Bayersdörfer, Hamburg (DE)

(73) Assignee: Henkel AG & Co. KGAA, Dusseldorf (DE)

( * ) Notice: Subject to any disclaimer, the term of this patent is extended or adjusted under 35 U.S.C. 154(b) by 238 days.

(21) Appl. No.: 12/753,161

(22) Filed: Apr. 2, 2010

(65) Prior Publication Data

US 2010/0189678 A1    Jul. 29, 2010

Related U.S. Application Data

(63) Continuation of application No. PCT/EP2008/062452, filed on Sep. 18, 2008.

(30) Foreign Application Priority Data

Oct. 4, 2007   (DE) .................. 10 2007 047 687

(51) Int. Cl.
*A61K 8/81* (2006.01)
*A61Q 5/06* (2006.01)

(52) U.S. Cl.
CPC .......... *A61Q 5/06* (2013.01); *A61K 8/8152* (2013.01); *A61K 8/8164* (2013.01); *A61K 8/817* (2013.01); *A61K 2800/5424* (2013.01); *A61K 2800/5428* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 3,753,968 A | 8/1973 | Ward | |
| 5,773,595 A | 6/1998 | Weuthen et al. | |
| 6,235,913 B1 | 5/2001 | Raths et al. | |
| 6,375,932 B1 * | 4/2002 | Hiwatashi et al. | 424/47 |
| 2005/0130865 A1 | 6/2005 | Schmid et al. | |
| 2007/0202069 A1 * | 8/2007 | Tamareselvy et al. | 424/70.12 |
| 2008/0085253 A1 * | 4/2008 | Nguyen et al. | 424/70.12 |
| 2008/0182773 A1 * | 7/2008 | Gauweiler et al. | 510/475 |
| 2010/0028272 A1 * | 2/2010 | Knappe et al. | 424/47 |

FOREIGN PATENT DOCUMENTS

| | | |
|---|---|---|
| AU | 730455 B2 | 5/2000 |
| DE | 3139438 A1 | 4/1983 |
| DE | 19756454 C1 | 6/1999 |
| DE | 10240757 A1 | 7/2003 |
| EP | 0671161 A1 | 9/1995 |
| WO | 9819653 A | 5/1998 |
| WO | 9913827 A1 | 3/1999 |
| WO | WO 2006100299 A1 * | 9/2006 |

OTHER PUBLICATIONS

Guidelines for the Declaration of Ingredients in Cosmetics, (Leitfadens zur Inhaltsstoffdeklaration kosmetischer Mittel). published by the German Cosmetics, Toiletry, Perfumery and Detergent Association e.V., 3rd edition, p. 44, (1996).

Römp-Lexikon. Chemie. George Thieme Verlag, vol. 10, 1997, pp. 1764.

* cited by examiner

*Primary Examiner* — H. Sarah Park
(74) *Attorney, Agent, or Firm* — Ingrassia Fisher & Lorenz, P.C.

(57) ABSTRACT

Cosmetics, particularly styling agents, containing at least one copolymer A composed of at least one monomer A1 chosen from acrylic acid, methacrylic acid, alkyl acrylates, and alkyl methacrylates, and at least one amphoteric monomer A2 chosen from (meth)acryloyl alkyl betaines and (meth)acryloyl alkyl amine oxides, and at least one film-forming and/or stabilizing anionic copolymer B in a cosmetically acceptable carrier. Also disclosed is the use of said cosmetics for temporarily shaping hair.

3 Claims, No Drawings

HAIR PREPARATION CONTAINING TWO COPOLYMERS

CROSS REFERENCE TO RELATED APPLICATIONS

The present application is a continuation of International Application No. PCT/EP2008/062452 filed 18 Sep. 2008, which claims priority to German Patent Application No. 10 2007 047 687.8 filed 4 Oct. 2007, both of which are incorporated herein by reference.

The invention relates to cosmetics used for shaping keratin-containing fibers. The cosmetics are manufactured by combining two different acrylate type copolymers having a high resistance to water and perspiration while at the same time are easily rinsed off.

Keratin-containing fibers include all animal hair (e.g., wool, horsehair, angora hair, furs, feathers and products or fabrics produced from them). However, keratin-containing fibers preferably concern human hair.

Use of polymers in all kinds of cosmetics is widespread. For example, they are found in both skin and hair treatment agents, in agents that are directly rinsed out or rinsed off again after their application (referred to as "rinse-off" products), as well as in agents that are left on the skin or hair (referred to as "leave-on" agents). In this regard, the polymers are employed for a variety of reasons and each specific property of the polymers is utilized. Thickening or caring properties of the polymers are frequently the focus in skin treatment agents, shampoos, hair rinses and hair tonics. In addition to these properties, film forming and/or setting effects are required in agents for the temporary shaping of keratin-containing fibers (hereinafter also called styling agents). Polymers also often serve as auxiliaries in order to improve or even make possible the deposition and fixing of other active substances and ingredients onto the skin or hair. Thus, for example, rubbing fastness and consistency of coloration can be increased by adding suitable polymers to hair dyes.

Often cosmetics include single polymers specially tailored to produce a specific effect. If various effects are to be produced, then a plurality of polymers can be added. However, if too many different polymers are added, this can lead to a series of drawbacks. Formulation problems can arise, for example, because the polymers react with one another or with other ingredients of the agent, resulting in precipitations or decompositions. Certain polymers also tend to continually precipitate out onto skin and particularly onto hair so that they are not completely removed by normal washing, causing an unwanted accumulation of the polymer and thereby a subsequent burden to the skin or hair.

Accordingly, there is a need for polymers or suitable combinations of fewer polymers, which simultaneously exhibit as many as possible of the desired properties.

For example, in a styling agent, added polymers need to afford a high degree of hold to the treated hair. However, in addition to a high degree of hold, styling agents must fulfill a whole series of additional requirements. These requirements can be broadly subdivided into their properties on the hair, properties of the formulation (e.g., properties of the foam, gel or sprayed aerosol), and properties concerning handling of the styling agent, with particular importance attached to the properties on the hair. In addition to low stickiness and a balanced conditioning effect, there is the resistance of the hold towards moisture and perspiration. Furthermore, a styling agent should be universally applicable for as many types of hair as possible. If the styling agent is a gel or a paste, then the polymers should also exhibit thickening properties. Finally, the styling agent at the end of the application must leave as little residue as possible and be able to be easily washed out of the hair by conventional shampooing.

Accordingly, the present invention provides suitable polymer combinations that lend optimal properties to cosmetics even without the addition of further active substances. In particular, the polymer combinations exhibit thickening and film forming and/or setting properties. Styling agents comprising the polymers exhibit a very high degree of hold, without compromising flexibility and good moisture resistance, for example, towards ambient humidity, rain as well as towards perspiration. At the same time the styling agent is easily washed out by conventional shampoos.

It has now been surprisingly found that this can be achieved by a combination of specific amphoteric and anionic polymers.

Accordingly, in one embodiment the present invention is a cosmetic that comprises, in an acceptable carrier,
a) at least one copolymer A made up from
 at least one monomer A1 chosen from acrylic acid, methacrylic acid, acrylic acid alkyl esters and methacrylic acid alkyl esters, and
 at least one amphoteric monomer A2 chosen from (meth) acryloyl alkyl betaines of Formula A2-I

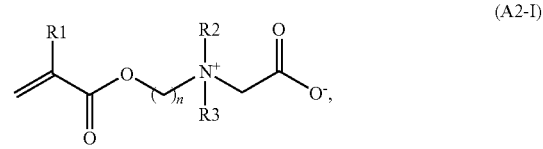

(A2-I)

and (meth)acryloyl alkylamine oxides of Formula A2-II

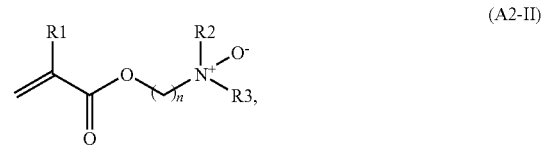

(A2-II)

wherein in Formulae A2-I and A2-II, R1 is H or $CH_3$, R2 and R3 are independently an optionally branched $C_1$-$C_{10}$ alkyl, and n is a whole number from 1 to 20, and
b) at least one film-forming and/or setting anionic copolymer B different from copolymer A.

Film forming and/or setting anionic polymers B are known. The same is true for copolymers A and their use as film-forming and/or setting polymers. It has now been surprisingly found that an appropriate combination of both types of polymer provides self-thickening properties, with the excellent film forming and/or setting properties of the individual polymers also being augmented. Styling agents comprising a combination of these polymers exhibit a synergistic increase in the degree of hold and moisture resistance, without any impairment to their ability to be washed out.

Cosmetics according to the invention comprise at least one copolymer A as a first ingredient.

In the context of the present invention, copolymers A made up from the cited monomers include only those copolymers that, in addition to polymer units resulting from the incorporation of the cited monomers A1 and A2 into the copolymer, comprise no more than about 5 wt. %, preferably no more than about 1 wt. % of polymer units that trace back to the incorporation of other monomers. In one embodiment, copolymers A are preferably made up from polymer units resulting from the polymerization of just the cited monomers A1 and A2 into the copolymer.

Preferred monomers A1 include acrylic acid, methacrylic acid, $C_{1-20}$ alkyl esters of acrylic acid and $C_{1-20}$ alkyl esters of methacrylic acid.

Monomer A1 is particularly preferably acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, methacrylic acid isopropyl ester, acrylic acid octyl ester, methacrylic acid octyl ester, acrylic acid decyl ester, methacrylic acid dodecyl ester, acrylic acid lauryl ester, methacrylic acid lauryl ester, acrylic acid myristyl ester, methacrylic acid myristyl ester, acrylic acid cetyl ester, methacrylic acid cetyl ester, acrylic acid stearyl ester, methacrylic acid stearyl ester, acrylic acid eicosyl ester and methacrylic acid eicosyl ester, quite particularly preferably from acrylic acid, methacrylic acid, acrylic acid methyl ester, methacrylic acid methyl ester, acrylic acid ethyl ester, methacrylic acid ethyl ester, acrylic acid lauryl ester, methacrylic acid lauryl ester, acrylic acid stearyl ester or methacrylic acid stearyl ester.

Preferred monomers A2 include (meth)acryloyl alkyl betaines of Formula A2-I and (meth)acryloyl alkylamine oxides of Formula A2-II, wherein R2 and R3 are independently methyl, ethyl, n-propyl, i-propyl, n-butyl, i-butyl or t-butyl, particularly methyl.

Preferred monomers A2 further include (meth)acryloyl alkyl betaines of Formula A2-I and (meth)acryloyl alkylamine oxides of Formula A2-II, wherein n is a whole number from 1 to 5, preferably a whole number from 1 to 3, and particularly preferably 2.

Monomers A2 also preferably include (meth)acryloyl alkyl betaines of Formula A2-I and (meth)acryloyl alkylamine oxides of Formula A2-II, wherein R1 is methyl.

A monomer A2 according to Formula A24 or A2-II is quite particularly preferred wherein R1, R2 and R3 are methyl and n is 2.

In a first preferred embodiment, the agent according to the invention comprises at least one copolymer A that is made up from at least one monomer A1 chosen from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and a monomer A2 according to Formula A2-I, wherein R1, R2 and R3 are methyl and n is 2.

Suitable copolymers (INCI Name: Methacryloyl ethyl betaine Acrylates Copolymer) are known and available, for example, under the names Diaformer Z-400, Diaformer Z-AT, Diaformer Z-301N, Diaformer Z-SM and Diaformer Z-W from Clariant, the names Yukaformer 202, Yukaformer 204, Yukaformer 206 and Yukaformer 301 from Mitsubishi, and the names MIHAPOL® PBS-50, MIHAPOL® PBM-40 and MIHAPOL® PBG-30 from Miwon Commercial Co., Ltd.

In a second preferred embodiment, the agent according to the invention comprises at least one copolymer A that is made up from at least two monomers A1, wherein the first monomer is acrylic acid, methacrylic acid, acrylic acid methyl ester, methacrylic acid methyl ester, acrylic acid ethyl ester, or methacrylic acid ethyl ester, and the second monomer is acrylic acid stearyl ester or methacrylic acid stearyl ester, and a monomer A2 according to Formula A2-II, wherein R1, R2 and R3 are methyl and n is 2.

These copolymers are known and available, for example, under the name Diaformer Z-632 from Clariant, wherein the addition of Diaformer Z-632 is particularly preferred.

In a third preferred embodiment, the agent according to the invention comprises at least one copolymer A that is made up from at least three monomers A1, wherein the first monomer is, acrylic acid, methacrylic acid, acrylic acid methyl ester, methacrylic acid methyl ester, acrylic acid ethyl ester, or methacrylic acid ethyl ester, the second monomer is acrylic acid lauryl ester or methacrylic acid lauryl ester, and the third monomer is acrylic acid stearyl ester or methacrylic acid stearyl ester, and a monomer A2 according to Formula A2-II, wherein R1, R2 and R3 are methyl and n is 2.

Corresponding copolymers are likewise known and available, for example, under the names Diaformer® Z-651N, Diaformer® Z-731N, Diaformer® Z-711N, Diaformer® Z-712N and Diaformer® Z-712W from Clariant.

It is also possible that agents according to the invention comprise a mixture of at least two of the copolymers A which are added according to the three preferred embodiments just described.

Agents according to the invention comprise copolymer A preferably in a quantity of about 0.01 to about 20 wt. %, preferably about 0.1 to about 15 wt. %, particularly preferably about 1.0 to about 12 wt. %, each based on total weight of the composition.

Agents according to the invention can also comprise a plurality of copolymers A, wherein the total amount of copolymer A is preferably no more than about 20 wt. %.

Copolymers A can be manufactured from the cited monomers by known polymerization methods and in general are commercially available.

For temporary shaping of the keratin-containing fibers, agents according to the invention comprise as a second ingredient at least one film-forming and/or setting anionic copolymer B different from copolymer A.

The film forming and/or setting anionic copolymer B is preferably copolymers formed from monomers containing carboxy and/or sulfone groups, especially acrylic acid, methacrylic acid, itaconic acid and their alkyl esters. Particularly preferred alkyl esters comprise $C_1$ to $C_{10}$ alkyl groups.

Preferred anionic copolymers B according to the invention are manufactured from acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, methacrylic acid isopropyl ester, acrylic acid butyl ester, methacrylic acid butyl ester, acrylic acid isobutyl ester, methacrylic acid isobutyl ester, acrylic acid t-butyl ester and methacrylic acid t-butyl ester.

Agents according to the invention particularly preferably comprises a methacrylic acid/ethyl acrylate copolymer as the film-forming and/or setting anionic copolymer B; the copolymer marketed by BASF AG under the name Luviflex® Soft (INCI name: Acrylates Copolymer) is particularly preferred.

The film forming and/or setting anionic copolymer B is preferably present in an amount of about 0.01 to about 20 wt. %, preferably about 0.1 to about 15 wt. %, particularly preferably about 1.0 to about 10 wt. %, based on total weight of the composition. Of course, agents according to the invention can also include a plurality of film-forming and/or setting anionic copolymers B, wherein the total amount of film-forming and/or setting anionic copolymers B is, however preferably no more than about 20 wt. %.

In order to achieve the desired properties of the agent according to the invention, the agent must include copolymer A as well as a film forming and/or setting anionic copolymer B that is different from copolymer A. In particular, the desirable combination of very strong hold and excellent moisture resistance with simultaneous good washing out performance can be achieved for styling agents in this way. It appears that an optimal property profile is produced when the agent comprises copolymer A and the film-forming and/or setting anionic copolymer B in a weight ratio of 1:20 to 20:1, preferably from 1:10 to 10:1, particularly preferably from 1:5 to 5:1, quite particularly preferably 1:2 to 2:1.

In addition to copolymer A and film forming and/or setting anionic copolymers B, the agents can further comprise all additional known film-forming and/or setting polymers. In this regard, these film-forming and/or setting polymers can be both permanently as well as temporarily cationic, anionic, amphoteric or non-ionic.

As polymers are often multifunctional, their functions cannot always be clearly and unequivocally distinguished from one another. This is particularly true for film forming and setting polymers. Here, reference is explicitly made to the fact that in the context of the present invention, both film forming and setting properties are included. As both properties are not completely independent from one other, the term "setting polymers" is also always understood to mean "film forming polymers" and vice versa.

Preferred properties of the film forming polymers include film formation. Film forming polymers refer to those polymers that, on drying, leave a continuous film on the skin, hair or nails. These types of film former can be used in the widest variety of cosmetic products, such as make up masks, make up, hair sets, hair sprays, hair gels, hair waxes, hair conditioners, shampoos or nail varnishes. Products which are sufficiently soluble in alcohol or water/alcohol mixtures are particularly preferred, so that they are present in completely dissolved form in compositions according to the invention. The film forming polymers can be of synthetic or natural origin.

According to the invention, film forming polymers further refer to those polymers that, when used in concentrations of 0.01 to 20 wt. % in aqueous, alcoholic or aqueous alcoholic solution, are able to separate out a transparent polymer film on the hair.

Exemplary suitable further synthetic, film forming, hair setting polymers include homopolymers or copolymers based on at least one of the following monomers: vinyl pyrrolidone, vinyl caprolactam, vinyl esters such as e.g. vinyl acetate, vinyl alcohol, acrylamide, methacrylamide, alkyl- and dialkyl acrylamide, alkyl- and dialkyl methacrylamide, alkyl acrylate, alkyl methacrylate, propylene glycol or ethylene glycol, wherein the alkyl groups of these monomers are preferably $C_1$ to $C_7$ alkyl groups, particularly preferably $C_1$ to $C_3$ alkyl groups.

Homopolymers of vinyl caprolactam, vinyl pyrrolidone or N-vinyl formamide may be cited as examples. Further suitable synthetic film forming, hair setting polymers include copolymers of vinyl pyrrolidone and vinyl acetate, terpolymers of vinyl pyrrolidone, vinyl acetate and vinyl propionate, polyacrylamides commercially under the trade names Akypomine® p 191 by Kao Chemicals (formerly CHEM-Y GmbH), Emmerich, or Sepigel® 305 by Seppic; polyvinyl alcohols commercially available under the trade names Elvanol® by Du Pont or Vinol® 523/540 by Air Products as well as polyethylene glycol/polypropylene glycol copolymers, commercially available, for example, under the trade name Ucon® by Union Carbide.

Particularly inventively preferred film-forming and/or setting copolymers are for example marketed under the trade names Luviquat® Supreme (INCI name: Polyquaterium-68) from Firma BASF AG, Ludwigshafen, under the name Acudyne® LT-120 (INCI name: Acrylates/C1-2 Succinates/Hydroxyacrylates Copolymer) from Rohm and Haas, Personal Care, and under the name Amphomer® (INCI name: Octylacrylamide/Acrylates/Butylaminoethyl Methacrylate Copolymer) from National Starch.

Suitable natural film forming polymers include cellulose derivatives (e.g., hydroxypropyl cellulose with a molecular weight of 30,000 to 50,000 g/mol, commercially available under the trade name Nisso Sl® by Lehmann & Voss, Hamburg).

Setting polymers contribute to the hold and/or creation of hair volume and hair body of the whole hairstyle. These so-called setting polymers are also film forming polymers and therefore are generally typical substances used for styling hair treatment compositions such as hair sets, hair foams, hair waxes, hair sprays. The film formation can be in completely selected areas and bond only some fibers together.

Substances that additionally confer hydrophobic properties to the hair are preferred, as they reduce the tendency of the hair to absorb moisture (i.e., water). In this way the sagging of the tresses of hair is reduced, thereby ensuring a long-lasting style configuration and retention. The so-called curl-retention test is frequently used as the test method for this. Moreover, these polymeric substances can be successfully incorporated in leave-on and rinse-off hair conditioners or shampoos. As polymers are often multifunctional (i.e., show a plurality of desired end-use effects), a large number of polymers are found in many of the groups subdivided according to the mode of action, also in the CTFA Handbook.

In so far as the inventive agents comprise further film-forming and/or setting polymers, these are preferably added in a quantity of about 0.01 to about 20 wt. %, preferably about 0.1 to about 15 wt. %, based on total weight of the hair setting agent. Of course, a plurality of film forming and/or setting polymers can be comprised, wherein the total amount of additional film-forming and/or setting polymers is, however preferably no more than about 20 wt. %.

In a preferred embodiment, agents according to the invention comprise exclusively copolymer A as the film-forming and/or setting polymer and film-forming and/or setting anionic polymer B.

Agents according to the invention comprise the polymers in a cosmetically acceptable carrier.

Preferred cosmetically acceptable carriers include aqueous, alcoholic or aqueous alcoholic media containing at least about 10 wt. % water, based on total weight of the agent. In particular, lower alcohols containing 1 to 4 carbon atoms (e.g., ethanol and isopropanol), which are usually used for cosmetic purposes, can be used.

Organic solvents or mixture of solvents with a boiling point of less than about 400° C. can be used as an additional co-solvent in a quantity of about 0.1 to about 15 wt. %, preferably about 1 to about 10 wt. %, based on total weight of the agent. Particularly suitable additional co-solvents are unbranched or branched hydrocarbons such as pentane, hexane, isopentane, and cyclic hydrocarbons such as cyclopentane and cyclohexane. Additional particularly preferred water-soluble solvents include glycerine, ethylene glycol and propylene glycol in an amount of up to about 30 wt. %, based on total weight of the agent.

The agents preferably exhibit a pH of about 2 to about 11. The pH range is particularly preferably from about 2 to about 8. In the context of this publication, pH data refers to the pH at 25° C. unless otherwise stated.

Agents according to the invention can additionally comprise auxiliaries and additives typically incorporated into each cosmetic.

In particular, care substances may be mentioned as suitable auxiliaries and additives. They find use in both skin treatment agents and hair treatment agents, and depending on the choice of the care substance, they can be incorporated into, for example, creams, shampoos, hair rinses, gels, pump and aerosol sprays and foam products.

For example, silicone oil and/or silicone gum can be employed as the care substance. In a particular embodiment of the invention, the agents comprise at least one silicone oil and/or silicone gum.

Suitable silicone oils or silicone gums according to the invention include dialkyl and alkylarylsiloxanes such as dimethylpolysiloxane and methylphenylpolysiloxane, as well as their alkoxylated, quaternized or also anionic derivatives. Cyclic and linear polydialkylsiloxanes, their alkoxylated and/or aminated derivatives, dihydroxypolydimethylsiloxanes and polyphenylalkylsiloxanes are preferred.

Silicone oils afford the most varied effects. Thus, for example, they simultaneously influence dry and wet combability, the feel of dry and wet hair, as well as the gloss. The term, "silicone oils" is understood by one skilled in the art to mean organosilicon compounds having any of a plurality of structures. Among these are included the dimethiconols (S1). They can be linear, branched, cyclic or cyclic and branched. Linear dimethiconols can be represented by the following structural formula (S1-I):

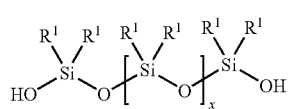
(S1-I)

Branched dimethiconols can be represented by the following structural formula (S1-II):

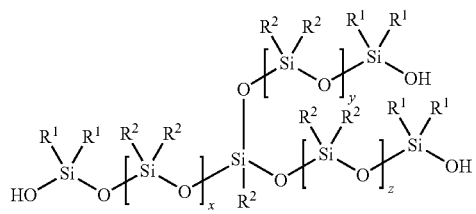
(S1-II)

In the above formulae, $R^1$ and $R^2$ are independently hydrogen, a methyl group, a $C_2$ to $C_{30}$ linear, saturated or unsaturated hydrocarbon group, a phenyl group and/or an aryl group. Non-limiting examples of $R^1$ and $R^2$ include alkyl groups such as methyl, ethyl, propyl, isopropyl, isopropyl, butyl, isobutyl, pentyl, isopentyl, neopentyl, amyl, isoamyl, hexyl, isohexyl and the like; alkenyl groups such as vinyl, halogenovinyl, alkylvinyl, allyl, halogenoallyl, and alkylallyl; cycloalkyl groups such as cyclobutyl, cyclopentyl, cyclohexyl and the like; phenyl groups; benzyl groups; halogenated hydrocarbon groups such as 3-chloropropyl, 4-bromobutyl, 3,3,3-trifluoropropyl, chlorocyclohexyl, bromophenyl, chlorophenyl and the like; as well as sulfur-containing groups such as mercaptoethyl, mercaptopropyl, mercaptohexyl, mercaptophenyl and the like. Preferably, $R^1$ and $R^2$ are an alkyl group that comprises 1 to about 6 carbon atoms; particularly preferably $R^1$ and $R^2$ are methyl. The numbers x, y and z are whole numbers and each independently range from 0 to 50,000. Molecular weights of the dimethiconols lie from about 1000 D to about 10,000,000 D. Viscosities range from about 100 to about 10,000,000 cPs (measured at 25° C. with a glass capillary viscosimeter following the Dow Corning Corporate Test Method CTM 0004 of 20 Jul. 1970). Preferred viscosities are from about 1000 to about 5,000,000 cPs, quite particularly preferred viscosities are from about 10,000 to about 3,000,000 cPs. The most preferred range is from about 50,000 to about 2,000,000 cPs.

The following commercial products are examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzene sulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401 DC (all from Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all from Dow Corning Corporation), Dub Gel Sl 1400 (Stearinerie Dubois Fils), HVM 4852 Emulsion (Crompton Corporation), Jeesilc 6056 (Jeen International Corporation), Lubrasil, Lubrasil DS (both from Guardian Laboratories), Nonychosine E, Nonychosine V (both from Exsymol), SanSurf Petrolatum-25, Satin Finish (both from Collaborative Laboratories, Inc.), Silatex-D30 (Cosmetic Ingredient Resources), Silsoft 148, Silsoft E-50, Silsoft E-623 (all from Crompton Corporation), SM555, SM2725, SM2765, SM2785 (all from GE Silicones), Taylor T-Sil CD-1, Taylor TME-4050E (all from Taylor Chemical Company), TH V 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all from Wacker-Chemie GmbH).

Dimethicones (S2) form the second group of silicones that can be included in the invention. They can be linear, branched, cyclic, or cyclic and branched. Linear dimethicones can be represented by the following structural formula (S2-I):

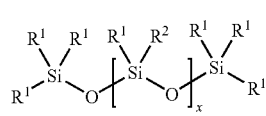
(S2-I)

Branched dimethicones can be represented by the structural formula (S2-II):

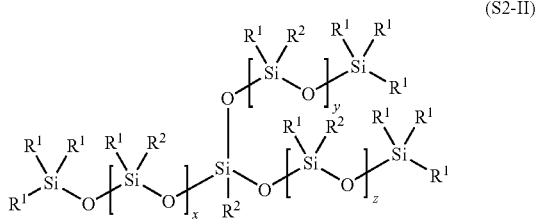
(S2-II)

In the above formulae, $R^1$ and $R^2$ are independently hydrogen, a methyl group, a $C_2$ to $C_{30}$ linear, saturated or unsaturated hydrocarbon group, a phenyl group and/or an aryl group. Non-limiting examples of $R^1$ and $R^2$ include alkyl groups such as methyl, ethyl, propyl, isopropyl, isopropyl, butyl, isobutyl, pentyl, isopentyl, neopentyl, amyl, isoamyl, hexyl, isohexyl and the like; alkenyl groups such as vinyl, halogenovinyl, alkylvinyl, allyl, halogenoallyl, alkylallyl; cycloalkyl groups such as cyclobutyl, cyclopentyl, cyclohexyl and the like; phenyl groups; benzyl groups; halogenated hydrocarbon groups such as 3-chloropropyl, 4-bromobutyl, 3,3,3-trifluoropropyl, chlorocyclohexyl, bromophenyl, chlorophenyl and the like; as well as sulfur-containing groups such as mercaptoethyl, mercaptopropyl, mercaptohexyl, mercaptophenyl and the like. Preferably, $R^1$ and $R^2$ are an alkyl group that comprises 1 to about 6 carbon atoms; particularly preferably $R^1$ and $R^2$ are methyl. The numbers x, y and z are whole numbers independently ranging from 0 to 50,000. Molecular weights of the dimethicones lie from about 1000 D to about 10,000,000 D. Viscosities range from about 100 to about 10,000,000 cPs (measured at 25° C. with a glass capillary viscosimeter following the Dow Corning Corporate Test Method CTM 0004 of 20 Jul. 1970). Preferred viscosities are from about 1000 to about 5,000,000 cPs; particularly preferred viscosities are from about 10,000 to about 3,000,000 cPs. Quite particularly preferably, the viscosity is in the range from about 50,000 to about 2,000,000 cPs.

Dimethicone copolyols (S3) represent a further group of suitable silicones. Dimethicone copolyols can be illustrated by the following structural formulae:

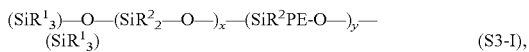 (S3-I),

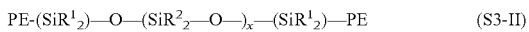 (S3-II)

Branched dimethicone copolyols can be represented by the following structural formula (S3-III):

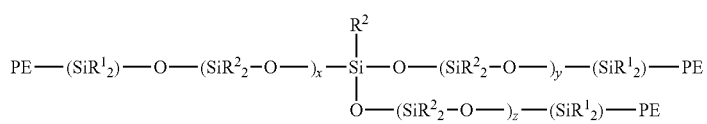
(S3-III)

or by the structural formula (S3-IV):

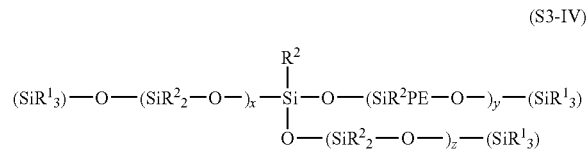
(S3-IV)

In the above formulae, $R^1$ and $R^2$ are independently hydrogen, a methyl group, a $C_2$ to $C_{30}$ linear, saturated or unsaturated hydrocarbon group, a phenyl group and/or an aryl group. Non-limiting examples of $R^1$ and $R^2$ include alkyl groups such as methyl, ethyl, propyl, isopropyl, isopropyl, butyl, isobutyl, pentyl, isopentyl, neopentyl, amyl, isoamyl, hexyl, isohexyl and the like; alkenyl groups such as vinyl, halogenovinyl, alkylvinyl, allyl, halogenoallyl, alkylallyl; cycloalkyl groups such as cyclobutyl, cyclopentyl, cyclohexyl and the like; phenyl groups; benzyl groups; halogenated hydrocarbon groups such as 3-chloropropyl, 4-bromobutyl, 3,3,3-trifluoropropyl, chlorocyclohexyl, bromophenyl, chlorophenyl and the like; as well as sulfur-containing groups such as mercaptoethyl, mercaptopropyl, mercaptohexyl, mercaptophenyl and the like. Preferably, $R^1$ and $R^2$ are an alkyl group that comprises 1 to about 6 carbon atoms; particularly preferably $R^1$ and $R^2$ are methyl. PE represents a polyoxyalkylene group. Preferred PE groups are derived from ethylene oxide, propylene oxide and glycerine. The numbers x, y and z are whole numbers independently ranging from 0 to 50,000. Molecular weights of the dimethicone copolyols lie from about 1000 D to about 10,000,000 D. Viscosities range from about 100 to about 10,000,000 cPs (measured at 25° C. with a glass capillary viscosimeter following the Dow Corning Corporate Test Method CTM 0004 of 20 Jul. 1970). Preferred viscosities are from about 1000 to about 5,000,000 cPs; quite particularly preferred viscosities are from about 10,000 to about 3,000,000 cPs. The most preferred range is from about 50,000 to about 2,000,000 cPs.

Suitable dimethicone copolyols are commercially available and marketed, for example, by Dow Corning under the trade name Dow Corning® 5330 Fluid.

According to the invention, the dimethiconols, dimethicones and/or dimethicone copolymers can also be present as an emulsion. The corresponding emulsions of the dimethiconols, dimethicones and/or dimethicone copolymers can be produced after production of the corresponding dimethiconols, dimethicones and/or dimethicone copolymers using typical emulsification processes known to one skilled in the art. Cationic, anionic, non-ionic or zwitterionic surfactants and emulsifiers can be used as auxiliaries and adjuvants for production of the corresponding emulsions. Alternatively, emulsions of the dimethiconols, dimethicones and/or dimethicone copolymers can be produced directly by an emulsion polymerization process. These types of processes are also well known to the person skilled in the art.

When the dimethiconols, dimethicones and/or dimethicone copolymers are used as an emulsion, the droplet size of the emulsified particles can range from about 0.01 to about 10,000 μm, preferably about 0.01 to about 100 μm, particularly preferably about 0.01 to about 20 μm and quite particularly preferably about 0.01 to about 10 μm. Particle size is determined by the light scattering method.

If branched dimethiconols, dimethicones and/or dimethicone copolymers are used, here the branching is greater than any branching that may results from impurities in the respective monomers. Accordingly, in the context of the present invention, the degree of branching is understood to be about 0.01% or greater for branched Dimethiconols, Dimethicones and/or Dimethicone copolymers. The degree of branching is preferably about 0.1% or greater, and quite particularly preferably about 0.5% or greater. The degree of branching is determined from the ratio of the unbranched monomers to the branched monomers (i.e., the amount of tri and tetrafunctional siloxanes). According to the invention, both low-branched and highly branched dimethiconols, dimethicones and/or dimethicone copolymers can be quite particularly preferred.

Further suitable silicones include amino functional silicones (S4), especially silicones compiled under the INCI name Amodimethicone. These are understood to be silicones that possess at least one, optionally substituted, amino group.

Such silicones can be described, for example, by the Formula (S4-I):

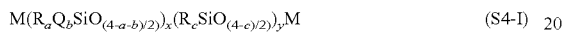
$$M(R_aQ_bSiO_{(4-a-b)/2})_x(R_cSiO_{(4-c)/2})_yM \quad (S4\text{-}I)$$

wherein, in the above formula R is a hydrocarbon or a hydrocarbon group with 1 to 6 carbon atoms, Q is a polar group of the general formula —R'Z, wherein $R^1$ is a divalent, linking group that is bonded to hydrogen and Z is made up of carbon atoms and hydrogen atoms, carbon-, hydrogen- and oxygen atoms or carbon-, hydrogen- and nitrogen atoms, or Z is an organic amino functionalized group having at least one amino functional group; "a" is a value in the range of about 0 to about 2, "b" is a value in the range of about 1 to about 3; "a"+"b" is less than or equal to 3; "c" is a number in the range of about 1 to about 3; x is a number in the range of about 1 to about 2000, advantageously from about 3 to about 50 and most preferably from about 3 to about 25; y is a number in the range of about 20 to about 10,000, advantageously from about 125 to about 10,000 and most preferably from about 150 to about 1000; and M is a suitable silicone end-group known in the prior art, preferably trimethylsiloxy. Non-limiting examples of R include alkyl groups such as methyl, ethyl, propyl, isopropyl, isopropyl, butyl, isobutyl, amyl, isoamyl, hexyl, isohexyl and the like; alkenyl groups such as vinyl, halogenovinyl, alkylvinyl, allyl, halogenoallyl, alkylallyl; cycloalkyl groups such as cyclobutyl, cyclopentyl, cyclohexyl and the like; phenyl groups; benzyl groups; halogenated hydrocarbon groups such as 3-chloropropyl, 4-bromobutyl, 3,3,3-trifluoropropyl, chlorocyclohexyl, bromophenyl, chlorophenyl and the like; as well as sulfur-containing groups such as mercaptoethyl, mercaptopropyl, mercaptohexyl, mercaptophenyl and the like. Preferably, R is an alkyl group having 1 to about 6 carbon atoms; and most preferably R is methyl. Examples of $R^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$C(O)OCH$_2$CH$_2$—, —C$_6$H$_4$C$_6$H$_4$—, —C$_6$H$_4$CH$_2$C$_6$H$_4$—, and —(CH$_2$)$_3$C(O)SCH$_2$CH$_2$—.

When Z is an organic, amino functional group having at least one functional amino group, a possible formula for Z is NH(CH$_2$)$_z$NH$_2$, wherein z is a whole number from 1 to 50. Another possible formula for Z is —NH(CH$_2$)$_z$(CH$_2$)$_z$NH(CH$_2$)$_{zz}$, wherein z and zz independently are a whole number from 1 to 50, wherein this structure includes diamino ring structures such as piperazinyl. Particularly preferably, Z is a —NHCH$_2$CH$_2$NH$_2$ group. Another possible formula for Z is —N(CH$_2$)$_z$NX$^1$X$^2$ or —NX$^1$X$^2$, wherein $X^1$ and $X^2$ are independently hydrogen or a hydrocarbon group containing 1 to about 6 carbon atoms.

Q is quite particularly preferably a polar, amino functional group of the Formula —CH$_2$CH$_2$CH$_2$NHCH$_2$CH$_2$NH$_2$.

The molar ratio of $R_aQ_b$ SiO$_{(4-a-b)/2}$ units to $R_cSiO_{(4-c)/2}$ units is in the range from about 1:2 to about 1:65, preferably from about 1:5 to about 1:65 and particularly preferably from about 1:15 to about 1:20. If one or a plurality of silicones of the above Formula is added, then the different variable substituents in the above Formula for the different silicone components that are present in the silicone mixture can be different.

Preferred amino functional silicones correspond to the Formula (S4-II)

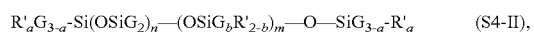
$$R'_aG_{3-a}\text{-}Si(OSiG_2)_n\text{---}(OSiG_bR'_{2-b})_m\text{---}O\text{---}SiG_{3-a}\text{-}R'_a \quad (S4\text{-}II),$$

wherein:

G is —H, a phenyl group, —OH, —O—CH$_3$, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$;

a is a number from 0 to 3, particularly 0;

b is a number from 0 to 1, particularly 1, m and n are numbers whose sum (m+n) is from 1 to 2000, preferably from 50 to 150, wherein n preferably assumes values of 0 to 1999, particularly 49 to 149, and m preferably assumes values of 1 to 2000, particularly 1 to 10, R' is a monovalent group chosen from

—N(R")—CH$_2$—CH$_2$—N(R")$_2$

—N(R")$_2$

N$^+$(R")$_3$A$^-$

—N$^+$H(R")$_2$A$^-$

—N$^+$H$_2$(R")A$^-$

—N(R")—CH$_2$—CH$_2$—N$^+$R"H$_2$A$^-$, wherein each R" stands for the same or different groups from —H, -phenyl, -benzyl, C$_{1-20}$ alkyl groups, preferably —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, and A$^-$ is an anion preferably chosen from chloride, bromide, iodide or methosulfate.

Particularly preferred amino functional silicones correspond to the Formula (S4-III)

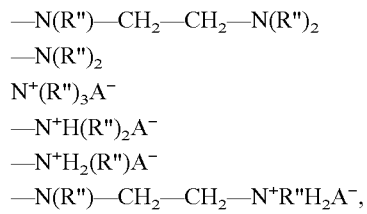

(S4-III)

wherein m and n are numbers whose sum (m+n) is from 1 to 2000, preferably from 50 to 150, wherein n preferably assumes values of 0 to 1999, particularly from 49 to 149, and m preferably assumes values of 1 to 2000, particularly 1 to 10.

These silicones are designated according to INCI nomenclature as Trimethylsilylamodimethicones.

Further amino functional silicones of the Formula (S4-IV) are particularly preferred

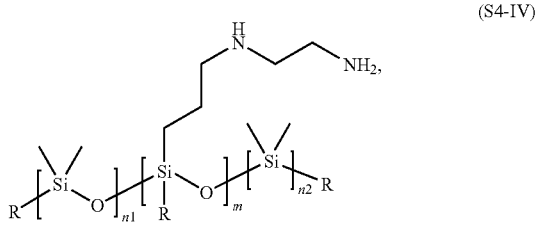

(S4-IV)

wherein R is —OH, —O—CH₃ or a —CH₃ group, and m, n1 and n2 are numbers whose sum (m+n1+n2) is from 1 to 2000, preferably from 50 to 150, wherein the sum (n1+n2) preferably assumes values of 0 to 1999 and particularly from 49 to 149 and m preferably assumes values of 1 to 2000, particularly 1 to 10.

These silicones are designated as Amodimethicones according to INCI nomenclature and are commercially available, for example, in the form of an emulsion as the product Dow Corning® 949 in a mixture with a cationic and a non-ionic surfactant.

Preferably, amino functional silicones are employed which have an amine number of about 0.25 meq/g or greater, preferably about 0.3 meq/g or greater, and particularly preferably about 0.4 meq/g or greater. The amine number stands for milliequivalents of amine per gram of amino functional silicone. It can be measured by titration and is also reported with the unit mg KOH/g.

Further suitable silicones include, for example
oligomeric polydimethylcyclosiloxanes (INCI name: Cyclomethicones), especially the tetrameric and the pentameric compound, commercially available as the products DC 245 Fluid, DC 344 or DC 345 by Dow Corning,
hexamethyldisiloxane (INCI name: Hexamethyldisiloxane), commercially available as the product marketed under the trade name Abil® K 520,
polyphenylmethylsiloxane (INCI name: Phenyl Trimethicone), commercially available as the product DC 556 Cosmetic Grade Fluid from Dow Corning,
esters and partial esters of silicone-glycol copolymers, commercially available by Fanning under the trade name Fancorsil® LIM (INCI name: Dimethicone Copolyol Meadowfoamate),
anionic silicone oils, commercially available as the product Dow Corning® 1784.

According to a preferred embodiment, compositions according to the invention include at least two different silicone derivatives, in particular, a combination of a volatile and a non-volatile silicone. Volatile silicones are those having a volatility that is the same or greater than the volatility of cyclic, pentameric dimethylsiloxane. Such combinations are commercially available (e.g. Dow Corning® 1401, Dow Corning® 1403 and Dow Corning® 1501, each being mixtures of a Cyclomethicone and a Dimethiconol).

Preferred mixtures of different silicones include Dimethicones and Dimethiconols, linear Dimethicones and cyclic Dimethiconols. A quite particularly preferred mixture of silicones consists of at least one cyclic Dimethiconol and/or Dimethicone, at least one additional non-cyclic Dimethicone and/or Dimethiconol as well as at least one amino functional silicone.

If different silicones are used as a mixture, then the mixing ratio can be varied over a wide range. Preferably, however, all of the silicones used in the mixture are employed in a ratio of 5:1 to 1:5 in the case of a binary mixture. A ratio of 3:1 to 1:3 is particularly preferred. Quite particularly preferred mixtures comprise as far as possible all silicones comprised in the mixture in a ratio of about 1:1, each based on the added quantities in wt. %.

The compositions preferably comprise the silicones in amounts of about 1 to about 25 wt. %, particularly preferably in amounts of about 5 to about 20 wt. % and particularly preferably in amounts of about 7 to about 15 wt. %, based on total weight of the composition.

Although compositions according to the invention preferably comprise a silicone derivative as the conditioning component, it is also possible that the composition has at least one conditioner from another compound class instead of or in addition to the silicone component.

The composition can comprise, for example, at least one protein hydrolyzate and/or one of its derivatives as a care substance of another compound class.

Protein hydrolyzates are product mixtures obtained by acid-, base- or enzyme-catalyzed degradation of proteins (albumins). According to the invention, the term "protein hydrolyzates" is also understood to mean total hydrolyzates as well as individual amino acids and their derivatives as well as mixtures of different amino acids. Furthermore, according to the invention, polymers built up from amino acids and amino acid derivatives are understood to be included in the term protein hydrolyzates. The latter include polyalanine, polyasparagine, polyserine etc. Additional examples of usable compounds according to the invention are L-alanyl-L-proline, polyglycine, glycyl-L-glutamine or D/L-methionine-S-methyl sulfonium chloride. β-amino acids and their derivatives, like β-alanine, anthranilic acid or hippuric acid, can also be added according to the invention. Molecular weight of protein hydrolyzates utilizable according to the invention ranges from about 75 (the molecular weight of glycine) to about 200 000, preferably the molecular weight is about 75 to about 50,000, and quite particularly preferably about 75 to about 20,000 Dalton.

According to the invention, the added protein hydrolyzates can be of vegetal, as well as animal, marine or synthetic origin.

Animal protein hydrolyzates include elastin, collagen, keratin, silk protein, and milk protein hydrolyzates, which can also be present in the form of their salts. Such products are marketed, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm) and Kerasol (Croda).

The use of silk protein hydrolyzates is particularly interesting. Silk refers to the fibers from the cocoon of the mulberry silk spinner (*Bombyx mori* L.). Raw silk fibers consist of a double stranded fibroin. Sericin is the intercellular cement that holds these double strands together. Silk consists of 70-80 wt. % fibroin, 19-28 wt. % sericin, 0.5-1 wt. % fat and 0.5-1 wt. % colorants and mineral constituents.

Protein hydrolyzates of vegetal origin (e.g., soya-, almond-, pea-, potato- and wheat protein hyrolyzates), are available, for example, under the trade names Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

Although it is preferred to add the protein hydrolyzates as such, optionally other mixtures containing amino acids can also be added in their place. Likewise, it is possible to add derivatives of protein hydrolyzates (e.g., in the form of their fatty acid condensation products). Such products are marketed, for example, under the trade names Lamepon® (Cognis), Lexein® (Inolex), Crolastin® (Croda), Crosilk® (Croda) or Crotein® (Croda).

Naturally, the teaching according to the invention includes all isomeric forms, such as cis/trans isomers, diastereoisomers and chiral isomers.

According to the invention, it is also possible to employ a mixture of a plurality of protein hydrolyzates.

Compositions according to the invention comprise the protein hydrolyzates, for example, in concentrations of about 0.01 wt. % to about 20 wt. %, preferably about 0.05 wt. % up to about 15 wt. % and quite particularly preferably in amounts of about 0.05 wt. % up to about 5 wt. %, each based on total end-use preparation.

In addition, cationic surfactants are suitable as care substances of another class of compounds.

According to the invention, cationic surfactants of the quaternary ammonium type compounds, esterquats and amido amines are preferred. Preferred quaternary ammonium compounds are ammonium halides, particularly chlorides and bromides, such as alkyltrimethylammonium chlorides, dialkyldimethylammonium chlorides and trialkylmethylammonium chlorides (e.g., cetyltrimethylammonium chloride, stearyltrimethyl ammonium chloride, distearyldimethylammonium chloride, lauryldimethylammonium chloride, lauryldimethylbenzylammonium chloride and tricetylmethylammonium chloride), as well as imidazolium compounds known under the INCI names Quaternium-27 and Quaternium-83. Long alkyl chains of the abovementioned surfactants have preferably 10 to 18 carbon atoms.

Esterquats are known compounds having at least one ester function and also a quaternary ammonium group as structural elements. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. Such products are marketed, for example, under the trade names Stepantex®, Dehyquart® and Armocare®. The products Armocare® VGH-70, an N,N-bis(2-Palmitoyloxyethyl) dimethylammonium chloride, as well as Dehyquart® F-75, Dehyquart® C-4046, Dehyquart® L80 and Dehyquart® AU 35 are examples of such esterquats.

Alkylamido amines are normally manufactured by the amidation of natural or synthetic fatty acids and fatty acid fractions with dialkylamino amines. According to the invention, a particularly suitable compound from this substance group is represented by stearamidopropyldimethylamine, commercially available under the designation Tegamid® S 18.

The inventive compositions preferably include cationic surfactants in quantities of about 0.05 to about 10 wt. %, based on total end-use preparation. Quantities of about 0.1 to about 5 wt. % are particularly preferred.

Conditioning polymers are also suitable conditioners. Some conditioning polymers also exhibit film-forming and/or setting properties, and consequently can also be included in the list of suitable film-forming and/or setting polymers.

A first group of conditioning polymers are cationic polymers. Cationic polymers are polymers possessing a group in the main chain and/or side chain which can be "temporarily" or "permanently" cationic. "Permanently cationic" refers to those polymers which independently of the pH of the medium have a cationic group. These are generally polymers having a quaternary nitrogen atom in the form of an ammonium group, for example. Preferred cationic groups are quaternary ammonium groups. In particular, those polymers in which the quaternary ammonium groups are bonded through a $C_{1-4}$ hydrocarbon group to a polymer backbone of acrylic acid, methacrylic acid or their derivatives, have proved to be particularly suitable.

Homopolymers of the general formula (G1-I):

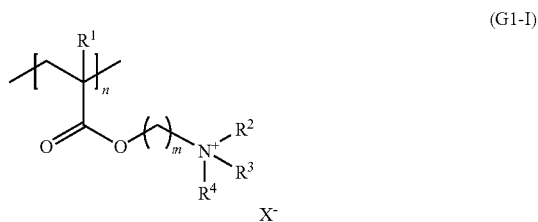

(G1-I)

wherein $R^1$ is —H or —$CH_3$, $R^2$, $R^3$ and $R^4$ independently are $C_{1-4}$ alkyl, -alkenyl or -hydroxyalkyl groups, m is 1, 2, 3 or 4, n is a natural number, and $X^-$ is a physiologically compatible organic or inorganic anion, as well as copolymers consisting essentially of the monomer units listed in formula (G1-I) as well as non-ionic monomer units, are particularly preferred cationic polymers. Regarding these polymers, those that are preferred in accordance with the invention meet at least one of the following conditions:

$R^1$ is a methyl group, $R^2$, $R^3$ and $R^4$ are methyl groups, and/or m=2.

Exemplary physiologically compatible counter ions $X^-$ include halide ions, sulfate ions, phosphate ions, methosulfate ions as well as organic ions such as lactate, citrate, tartrate and acetate ions. Halide ions are preferred, particularly chloride.

A particularly suitable homopolymer is the optionally crosslinked poly(methacryloyloxyethyltrimethylammonium chloride) with the INCI name Polyquaternium-37. Crosslinking can be effected, when desired, with the help of olefinically polyunsaturated compounds (e.g., divinylbenzene, tetraallyloxyethane, methylene bisacrylamide, diallyl ether, polyallyl polyglyceryl ether), or allyl ethers of sugars or sugar derivatives (e.g., erythritol, pentaerythritol, arabitol, mannitol, sorbitol, sucrose or glucose). Methylene bisacrylamide is a preferred crosslinking agent.

The homopolymer is preferably in the form of a non-aqueous polymer dispersion having a polymer content of about 30 wt. % or greater. Such polymer dispersions are commercially available under the names Salcare® SC 95 (ca. 50% polymer content, additional components: mineral oil (INCI name: Mineral Oil) and tridecyl-polyoxypropylene polyoxyethylene ether (INCI name: PPG-1-Trideceth-6)) and Salcare® SC 96 (ca. 50% polymer content, additional components: mixture of diesters of propylene glycol with a mixture of caprylic- and capric acid (INCI name: Propylene Glycol Dicaprylate/Dicaprate) and tridecyl-polyoxypropylene polyoxyethylene ether (INCI name: PPG-1-Trideceth-6)).

Copolymers with monomer units according to formula (G1-I) preferably comprise acrylamide, methacrylamide, $C_{1-4}$ alkyl esters of acrylic acid and $C_{1-4}$ alkyl esters of methacrylic acid as the non-ionic monomer units. Acrylamide is particularly preferred among these non-ionic monomers. These copolymers can also be crosslinked, as in the case of the above-described homopolymers. An inventively preferred copolymer is the crosslinked acrylamide/methacryloyloxyethyltrimethylammonium chloride copolymer. Such copolymers, in which the monomers are present in a weight ratio of about 20:80, are commercially available as an approximately 50% conc. non-aqueous polymer dispersion under the trade name Salcare® SC 92.

Further preferred cationic polymers are, for example—
- quaternized cellulose derivatives, commercially available under the trade names Celquat® and Polymer JR®. The compounds Celquat® H 100, Celquat® L 200 and Polymer JF® 400 are preferred quaternized cellulose derivatives,
- cationic alkyl polyglycosides according to DE-PS 44 13 686,
- cationized honey, for example the commercial product Honeyquat® 50,
- cationic guar derivatives, such as in particular the products marketed under the trade names Cosmedia® Guar and Jaguar®,
- polysiloxanes with quaternary groups, such as, for example, the commercially available products Q2-7224 (manufacturer: Dow Corning; a stabilized trimethylsilylamodimethicone), Dow Corning® 929 emulsion (comprising a hydroxylamino modified silicone, also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, Quaternium-80),
- polymeric dimethyldiallylammonium salts and their copolymers with esters and amides of acrylic acid and methacrylic acid. The commercially available products Merquat® 100 (poly(dimethyldiallylammonium chloride)) and Merquat® 550 (dimethyldiallylammonium chloride acrylamide copolymer) are examples of such cationic polymers,
- copolymers of vinyl pyrrolidone with quaternized derivatives of dialkylaminoalkyl acrylate and dialkylaminoalkyl methacrylate, such as vinyl pyrrolidone dimethylaminoethyl methacrylate copolymers quaternized with diethyl sulfate. Such compounds are commercially available under the trade names Gafquat® 734 and Gafquat® 755.
- Vinyl pyrrolidone vinylimidazolium methochloride copolymers, offered under the trade names Luviquat® FC 370, FC 550, FC 905 and HM 552,
- quaternized polyvinyl alcohol,
- as well as polymers containing quaternary nitrogen atoms in the main polymer chain, known under the names Polyquaternium 2, Polyquaternium 17, Polyquaternium 18 and Polyquaternium 27.

Polymers designated as Polyquaternium-24 (commercially available, for example, as Quatrisoft® LM 200) can also be employed as cationic polymers. Copolymers of vinyl pyrrolidone are also usable according to the invention, such as the commercially available products Copolymer 845 (manufacturer: ISP), Gaffix® VC 713 (manufacturer: ISP), Gafquat® ASCP 1011, Gafquat® HS110, Luviquat® 8155 and Luviquat® MS 370.

Further suitable cationic polymers according to the invention are the "temporarily cationic" polymers. These polymers usually comprise an amino group that is present at specific pH values as the quaternary ammonium group and is thus cationic. Chitosan and its derivatives, such as for example the commercially available Hydagen® CMF, Hydagen® HCMF, Kytamer® PC and Chitolam® NB/101 are preferred.

Inventively preferred cationic polymers are cationic cellulose derivatives and chitosan and its derivatives, particularly the commercial products Polymer® JR 400, Hydagen® HCMF and Kytamer® PC, cationic guar derivatives, cationic honey derivatives, in particular the commercial product Honeyquat® 50, cationic alkyl polyglycosides according to DE-PS 44 13 686 and polymers of the type Polyquaternium-37.

In addition, cationized protein hydrolyzates are considered as cationic polymers, wherein the base protein hydrolyzate can originate from animals (e.g., from collagen, milk or keratin), from plants (e.g., from wheat, maize, rice, potatoes, soya or almonds), from marine life (e.g., from fish collagen or algae), or from biotechnologically obtained protein hydrolyzates. Inventive cationic derivatives based on protein hydrolyzates can be obtained from the corresponding proteins by chemical, particularly alkaline or acidic, hydrolysis, by enzymatic hydrolysis, and/or a combination of both types of hydrolysis. Hydrolysis of proteins generally produces a protein hydrolyzate with a molecular weight distribution from about 100 Daltons up to several thousand Daltons. Cationic protein hydrolyzates are preferred whose base protein content has a molecular weight of about 100 to about 25,000 Daltons, preferably about 250 to about 5000 Daltons. Moreover, cationic protein hydrolyzates include quaternized amino acids and their mixtures.

Cationic protein hydrolyzates and derivatives based on plants are quite particularly preferred.

Preferably employed amphoteric polymers are polymers composed from (a) monomers with quaternary ammonium groups of the general Formula (II),

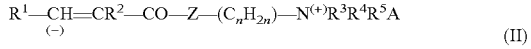

$$R^1-CH=CR^2-CO-Z-(C_nH_{2n})-N^{(+)}R^3R^4R^5 A^{(-)} \quad (II)$$

wherein $R^1$ and $R^2$ independently are hydrogen or a methyl group, and $R^3$, $R^4$ and $R^5$ independently are alkyl groups with 1 to 4 carbon atoms, Z is an NH-group or an oxygen atom, n is a whole number from 2 to 5, and $A^{(-)}$ is the anion of an organic or inorganic acid, and (b) monomeric carboxylic acids of the general formula (III),

$$R^6-CH=CR^7-COOH \quad (III)$$

wherein $R^6$ and $R^7$ independently are hydrogen or a methyl group.

According to the invention, these compounds can be added directly or in salt form, the latter being obtained, for example, by neutralization of the polymer with an alkali hydroxide. Quite particularly preferred are polymers which incorporate monomers of type (a), wherein $R^3$, $R^4$ and $R^5$ are methyl groups, Z is an NH-group and $A^{(-)}$ is a halide, methoxysulfate or ethoxysulfate ion. Acrylamido propyltrimethylammonium chloride is a particularly preferred monomer (a). Acrylic acid is preferably used as the monomer (b) in the cited polymers.

The inventive compositions preferably comprise conditioning, cationic and/or amphoteric polymers in an amount of about 0.01 to about 5 wt. %, particularly in a quantity of about 0.1 to about 2 wt. %, each based on total weight of the end-use preparation.

The composition according to the invention can further comprise at least one vitamin, one provitamin, one vitamin precursor and/or one of their derivatives as the conditioner.

According to the invention, preferred vitamins, provitamins and vitamin precursors are normally classified in the groups A, B, C, E, F and H.

Compositions according to the invention preferably comprise vitamins, provitamins and vitamin precursors from groups A, B, C, E and H.

Panthenol, pantolactone, pyridoxine and its derivatives, as well as nicotinamide and biotin are especially preferred.

D-panthenol is quite particularly preferably employed as a conditioner, optionally in combination with at least one of the abovementioned silicone derivatives.

Compositions according to the invention can further have at least one plant extract as a conditioner.

Usually, these extracts are manufactured by extraction of the whole plant. However, it can also be preferred to produce the extracts solely from blossoms and/or leaves of the plant.

With regard to the inventively usable plant extracts, reference is particularly made to extracts listed in the Table beginning on page 44 of the 3rd edition of the Guidelines for the Declaration of Ingredients in Cosmetics, (Leitfadens zur Inhaltsstoffdeklaration kosmetischer Mittel) published by the German Cosmetics, Toiletry, Perfumery and Detergent Association e.V. (IKW), Frankfurt.

Extracts from green tea, oak bark, stinging nettle, hamamelis, hops, henna, camomile, burdock root, field horsetail, hawthorn, linden flowers, almonds, aloe vera, spruce needles, horse chestnut, sandal wood, juniper, coconut, mango, apricot, lime, wheat, kiwi, melon, orange, grapefruit, sage, rosemary, birch, malva, lady's smock, common yarrow, thyme, lemon balm, rest-harrow, coltsfoot, marshmallow (althaea), meristem, ginseng and ginger are preferred.

The extraction composition used to prepare the cited plant extracts can be water or alcohols as well as their mixtures. Exemplary alcohols are lower alcohols such as ethanol and isopropanol, particularly polyhydroxy alcohols such as ethylene glycol, propylene glycol and butylene glycol, both as the sole extracting composition as well as in aqueous mixtures. Plant extracts based on water/propylene glycol in a ratio 1:10 to 10:1 have proven particularly suitable.

Carboxylic acids can also be used as a conditioner. In the present invention, short chain carboxylic acids can be particularly advantageous. Short chain carboxylic acids and their derivatives refer to carboxylic acids that can be saturated or unsaturated and/or linear or branched or cyclic and/or aromatic and/or heterocyclic and have a molecular weight of about 750 or less. Saturated or unsaturated or linear or branched carboxylic acids with a chain length of 1 to 16 carbon atoms in the chain can be preferred; those with a chain length of 1 up to 12 carbon atoms in the chain are quite particularly preferred.

Moreover, it is preferred to utilize 2-pyrrolidinone-5-carboxylic acid and its derivatives as the carboxylic acid. The sodium, potassium, calcium, magnesium or ammonium salts are particularly preferred, wherein the ammonium ion carries one to three $C_1$ to $C_4$ alkyl groups besides hydrogen. The sodium salt is quite particularly preferred. The quantities utilized in the products according to the invention are preferably about 0.05 to about 10 wt. %, based on total preparation, particularly preferably about 0.1 to about 5 wt. %, and especially preferably about 0.1 to about 3 wt. %.

In addition, it is preferred to add hydroxycarboxylic acids (e.g., the dihydroxy-, trihydroxy- and polyhydroxy carboxylic acids as well as the dihydroxy-, trihydroxy- and polyhydroxy di-, tri- and polycarboxylic acids). In addition to the hydroxycarboxylic acids, the hydroxycarboxylic acid esters as well as mixtures of hydroxycarboxylic acids and their esters and also polymeric hydroxycarboxylic acids and their esters can be quite particularly preferred. Preferred hydroxycarboxylic acid esters are, for example, fully esterified glycolic acid, lactic acid, malic acid, tartaric acid or citric acid. Additional fundamentally suitable hydroxycarboxylic acid esters are esters of β-hydroxypropionic acid, tartronic acid, D-gluconic acid, saccharic acid, mucic acid or glucuronic acid. Primary, linear or branched aliphatic alcohols containing 8-22 carbon atoms (i.e., fatty alcohols or synthetic fatty alcohols) are suitable alcohol moieties of these esters. Esters of $C_{12}$-$C_{15}$ fatty alcohols are particularly preferred in this respect. Esters of this type are commercially available, e.g. under the trade name Cosmacol® from Enichem, Augusta Industriale. Particularly preferred polyhydroxypolycarboxylic acids are polylactic acid and polytartaric acid as well as their esters.

Ectoin or ectoin derivatives, allantoin, taurine and/or bisabolol are also suitable conditioners.

Amino acids refer to the stereoisomeric forms (e.g., D- and L-forms) of the following compounds: asparagine, arginine, aspartic acid, glutamine, glutamic acid, β-alanine, γ-amino butyrate, $N_\epsilon$-acetyl lysine, $N_\delta$-acetyl ornithine, $N_\gamma$-acetyl diamino butyrate, $N_\alpha$-acetyl diamino butyrate, histidine, isoleucine, leucine, methionine, phenylalanine, serine, threonine and tyrosine.

L-amino acids are preferred. Amino acid groups are derived from the corresponding amino acid. The following amino acid groups are preferred: Gly, Ala, Ser, Thr, Val, β-Ala, γ-amino butyrate, Asp, Glu, Asn, Aln, $N_\epsilon$-acetyllysine, $N_\delta$-acetylornithine, $N_\gamma$-acetyl diamino butyrate, $N_\alpha$-acetyl diamino butyrate.

The abbreviated form of the amino acids conforms to generally accepted notation. The di- or tripeptide groups are acid amides in their chemical nature and decompose on hydrolysis into 2 or 3 amino acids. Amino acids in the di- or tripeptide group are bonded together through amide linkages.

Compositions according to the invention preferably comprise these conditioners in amounts of about 0.001 to about 2 wt. %, in particular about 0.01 to about 0.5 wt. %, each based on total preparation.

Mono- or oligosaccharides can also be incorporated as the conditioner into compositions according to the invention.

Monosaccharides and as oligosaccharides such as raw sugar, lactose and raffinose can be incorporated. According to the invention, monosaccharides are preferred. Monosaccharides preferably include compounds containing 5 or 6 carbon atoms.

Suitable pentoses and hexoses are, for example, ribose, arabinose, xylose, lyxose, allose, altrose, glucose, mannose, gulose, idose, galactose, talose, fucose and fructose. Arabinose, glucose, galactose and fructose are preferred carbohydrates; glucose is quite particularly preferred, and is suitable both in the D-(+)- or L-(−)-configuration or as the racemate.

In addition, derivatives of these pentoses and hexoses can also be incorporated according to the invention, such as the corresponding -onic and -uronic acids (sugar acids), sugar alcohols, and glycosides. Preferred sugar acids are gluconic acid, glucuronic acid, sugar acids, mannosugar acids and mucic acid. Preferred sugar alcohols are sorbitol, mannitol and dulcitol. Preferred glycosides are methyl glucosides.

As the incorporated mono- and oligosaccharides are usually obtained from natural raw materials such as starch, they generally possess configurations corresponding to these raw materials (e.g., D-glucose, D-fructose and D-galactose).

The compositions preferably comprise mono- or oligosaccharides in an amount of about 0.1 to about 8 wt. %, particularly preferably about 1 to about 5 wt. %, based on total end-use preparation.

The composition can further comprise at least one lipid as a conditioner.

According to the invention, suitable lipids are phospholipids (e.g., soy lecithin, egg lecithin and cephalin) as well as substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are commercialized, for example, by the Mona Company under the trade names Phospholipid EFA®, Phospholipid PTC® and Phospholipid SV®.

Compositions according to the invention preferably comprise the lipids in amounts of about 0.01 to about 10 wt. %, in particular about 0.1 to about 5 wt. %, based on total end-use preparation.

Oil bodies are also suitable as a conditioner.

Natural and synthetic cosmetic oil bodies include, for example:

vegetal oils. Examples of such oils are sunflower oil, olive oil, soya oil, rapeseed oil, almond oil, jojoba oil, orange oil, wheat germ oil, peach stone oil and the liquid parts of coconut oil. Other triglyceride oils such as the liquid fractions of beef tallow as well as synthetic triglyceride oils are also suitable, however.

liquid paraffin oils, isoparaffin oils and synthetic hydrocarbons as well as di-n-alkyl ethers containing a total of 12 to 36 carbon atoms, particularly 12 to 24 carbon atoms such as, for example, di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether and di-tert.butyl ether, diisopentyl ether, di-3-ethyldecyl ether, tert.butyl n-octyl ether, isopentyl n-octyl ether and 2-methylpentyl n-octyl ether. The commercial products 1,3-di-(2-ethylhexyl)cyclohexane (Cetiol® S) and di-n-octyl ether (Cetiol® OE) can be preferred.

Ester oils. Ester oils are understood to mean the esters of $C_6$-$C_{30}$ fatty acids with $C_2$-$C_{30}$ fatty alcohols. Monoesters of fatty acids with alcohols having 2 to 24 carbon atoms are preferred. Examples of fatty acids moieties utilized in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures, that e.g. result from cracking of natural fats and oils, from the oxidation of aldehydes from Roelen's Oxo Synthesis or from the dimerization of unsaturated fatty acids. Examples for the fatty alcohol moieties in the ester oils are isopropyl alcohol, caproyl alcohol, capryl alcohol, 2-ethylhexyl alcohol, 1-decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol as well as their technical mixtures, that e.g. result from the high pressure hydrogenation of industrial methyl esters based on fats and oils or aldehydes from Roelen's Oxo Synthesis as well as the monomer fraction of the dimerization of unsaturated fatty alcohols. According to the invention, isopropyl myristate (Rilanit® IPM), isononanoic acid-C16-18-alkyl ester (Cetiol® SN). 2-ethylhexyl palmitate (Cegesoft® 24), stearic acid 2-ethylhexyl ester (Cetiol® 868), Cetyl oleate, glycerine tricaprylate, cocofatty alcohol caprinate/-caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are particularly preferred.

Dicarboxylic acid esters such as di-n-butyl adipate, di-(2-ethylhexyl) adipate, di-(2-ethylhexyl) succinate and di-isotridecyl acetate as well as diol esters such as ethylene glycol dioleate, ethylene glycol di-isotridecanoate, propylene glycol di(2-ethylhexanoate), propylene glycol di-isostearate, propylene glycol di-pelargonate, butanediol di-isostearate, neopentyl glycol dicaprylate, symmetrical, unsymmetrical or cyclic esters of carbon dioxide with fatty alcohols (e.g., as described in DE-OS 197 56 454), glycerine carbonate or dicaprylyl carbonate (Cetiol® CC), trifatty acid esters of saturated and/or unsaturated linear and/or branched fatty acids with glycerine, fatty acid partial glycerides, which include monoglycerides, diglycerides and their industrial mixtures. When using industrial products, minor amounts of triglycerides may still be contained as a result of the production process. Partial glycerides preferably comply with the Formula (D4-I),

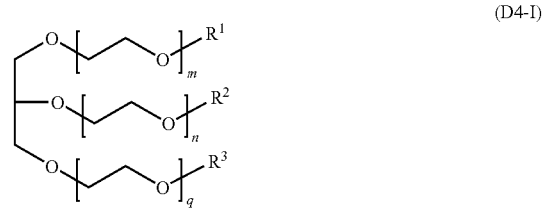

(D4-I)

wherein $R^1$, $R^2$ and $R^3$ independently are hydrogen or a linear or branched, saturated and/or unsaturated acyl group with 6 to 22 carbon atoms, preferably 12 to 18 carbon atoms, with the proviso that at least one of these groups stands for an acyl group and at least one of these groups stands for hydrogen. The sum of (m+n+q) is 0 or numbers from 1 to 100, preferably 0 or 5 to 25. Preferably, $R^1$ is an acyl group, $R^2$ and $R^3$ are hydrogen, and the sum of (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidonic acid, gadoleic acid, behenic acid and erucic acid as well as their industrial mixtures. Oleic acid monoglycerides are preferably employed.

The added quantity of natural and synthetic cosmetic oil bodies in compositions according to the invention is usually about 0.1 to about 30 wt. %, based on total end-use preparation, preferably about 0.1 to about 20 wt. % and particularly about 0.1 to about 15 wt. %.

Although each of the cited conditioners alone already provides a satisfactory result, in the context of the present invention all embodiments are included in which the composition comprises a plurality of conditioners even from different groups.

By addition of a UV filter, both the composition itself as well as the treated skin or hair can be protected against damage from UV radiation. Consequently, at least one UV filter is preferably added to the composition. Suitable UV filters are not generally limited with respect to structure and physical properties. Indeed, UV filters useful in cosmetics and having an absorption maximum in the UVA (315-400 nm), UVB (280-315 nm) or UVC (<280 nm) regions are suitable. UV filters having an absorption maximum in the UVB region, especially in the range from about 280 to about 300 nm, are particularly preferred.

Preferred UV-filters include substituted benzophenones, p-aminobenzoates, diphenylacrylates, cinnamates, salicylates, benzimidazoles and o-aminobenzoates.

The composition preferably comprises UV filters in quantities of about 0.01 to about 5 wt. %, based on total end-use preparation. Quantities of bout 0.1 to about 2.5 wt. % are preferred.

Depending on the type of the agent according to the invention, it may be necessary for them to comprise at least one surfactant. This is particularly the case for skin cleansers and shampoos. However, other agents such as hair rinses, hair tonics and certain styling agents, especially styling foams, can also comprise surfactants.

For example, cationic surfactants as described above can be added as suitable conditioners. The above descriptions are also valid in regard to preferred cationic surfactants and the added quantities.

In addition to or instead of cationic surfactants, the agents can further comprise surfactants or emulsifiers, wherein anionic as well as ampholytic and non-ionic surfactants and all types of known emulsifiers are suitable. The ampholytic or also amphoteric surfactants includes zwitterionic surfactants and ampholytes. The surfactants can already have an emulsifying action.

Suitable anionic surfactants include all anionic surface-active materials that are suitable for use on the human body. They are characterized by a water solubilizing anionic group such as a carboxylate, sulfate, sulfonate or phosphate group and a lipophilic alkyl group containing about 8 to 30 carbon atoms. In addition, the molecule may comprise glycol or polyglycol ether groups, ester, ether and amide groups as well as hydroxyl groups. Exemplary suitable anionic surfactants are, each in the form of the sodium, potassium and ammonium as well as the mono, di and trialkanolammonium salts containing 2 to 4 carbon atoms in the alkanol group, linear and branched fatty acids with 8 to 30 carbon atoms (soaps),
    ether carboxylic acids of the formula R—O—(CH$_2$—CH$_2$O)$_x$—CH$_2$—COOH, in which R is a linear alkyl group containing 8 to 30 carbon atoms and x=0 or 1 to 16,
    acyl sarcosides with 8 to 24 carbon atoms in the acyl group,
    acyl taurides with 8 to 24 carbon atoms in the acyl group,
    acyl isethionates with 8 to 24 carbon atoms in the acyl group,
    mono- and dialkyl esters of sulfosuccinic acid with 8 to 24 carbon atoms in the alkyl group and mono-alkyl polyoxyethyl esters of sulfosuccinic acid with 8 to 24 carbon atoms in the alkyl group and 1 to 6 oxyethylene groups,
    linear alkane sulfonates containing 8 to 24 carbon atoms,
    linear alpha-olefin sulfonates containing 8 to 24 carbon atoms,
    alpha-sulfo fatty acid methyl esters of fatty acids containing 8 to 30 carbon atoms,
    alkyl sulfates and alkyl polyglycol ether sulfates of formula R—O(CH$_2$—CH$_2$O)$_x$—OSO$_3$H, in which R is preferably a linear alkyl group containing 8 to 30 carbon atoms and x=0 or 1 to 12,
    mixtures of surface-active hydroxysulfonates,
    sulfated hydroxyalkyl polyethylene glycol ethers and/or hydroxyalkylene propylene glycol ethers,
    sulfonated unsaturated fatty acids with 8 to 24 carbon atoms and 1 to 6 double bonds,
    esters of tartaric acid and citric acid with alcohols, which represent the addition products of about 2-15 molecules of ethylene oxide and/or propylene oxide on fatty alcohols containing 8 to 22 carbon atoms,
    alkyl and/or alkenyl ether phosphates of Formula (E1-I),

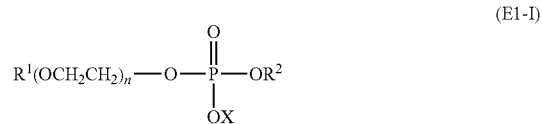

(E1-I)

wherein R$^1$ preferably is an aliphatic hydrocarbon group containing 8 to 30 carbon atoms, R$^2$ is hydrogen, a (CH$_2$CH$_2$O)$_n$R$^1$ group or X, n is a number from 1 to 10, and X is hydrogen, an alkali- or alkaline earth metal or NR$^3$R$^4$R$^5$R$^6$, with R$^3$ to R$^6$ independently are a C1 to C4 hydrocarbon group,
    sulfated fatty acid alkylene glycol esters of Formula (E1-II)

R$^7$CO(AlkO)$_n$SO$_3$M     (E1-II)

wherein R$^7$CO— is a linear or branched, aliphatic, saturated and/or unsaturated acyl group containing 6 to 22 carbon atoms, Alk is CH$_2$CH$_2$, CHCH$_3$CH$_2$ and/or CH$_2$CHCH$_3$, n is a number from 0.5 to 5, and M is a cation such as described in DE-OS 197 36 906,
    monoglyceride sulfates and monoglyceride ether sulfates of Formula (E1-III)

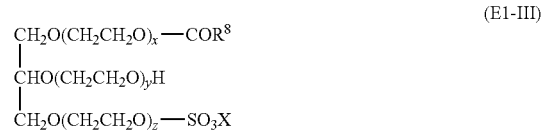

(E1-III)

wherein R$^8$CO is a linear or branched acyl group containing 6 to 22 carbon atoms, the sum of x, y and z is 0 or a number from 1 to 30, preferably 2 to 10, and X is an alkali or alkaline earth metal. Examples of suitable monoglyceride (ether) sulfates are the reaction products of lauric acid monoglyceride, cocoa fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid in the form of their sodium salts. Preferably, monoglyceride sulfates of Formula (E1-III) are added, in which R$^8$CO is a linear acyl group containing 8 to 18 carbon atoms,
    amido ether carboxylic acids,
    Condensation products of C$_8$-C$_{30}$ fatty alcohols with protein hydrolyzates and/or amino acids and their derivatives, commonly known as albumin fatty acid condensates, such as the Lamepon® types, Gluadin® types, Hostapon® KCG or Amisoft® types.

Preferred anionic surfactants are alkyl sulfates, alkyl polyglycol ether sulfates and ether carboxylic acids with 10 to 18 C atoms in the alkyl group and up to 12 glycol ether groups in the molecule, sulfosuccinic acid mono and dialkyl esters with 8 to 18 C atoms in the alkyl group and sulfosuccinic acid mono-alkyl polyoxyethyl esters with 8 to 18 C atoms in the alkyl group and 1 to 6 oxyethylene groups, monoglycerine disulfates, alkyl- and alkenyl ether phosphates as well as albumin fatty acid condensates.

Zwitterionic surfactants are those surface-active compounds that carry at least one quaternary ammonium group and at least one $—COO^{(-)}$ or $—SO_3^{(-)}$ group in the molecule. Particularly suitable zwitterionic surfactants are betaines such as N-alkyl-N,N-dimethylammonium glycinates, for example, cocoalkyl dimethylammonium glycinate, N-acylaminopropyl-N,N-dimethylammonium glycinates, for example, cocoacylaminopropyl dimethylammonium glycinate, and 2-alkyl-3-carboxymethyl-3-hydroxyethyl imidazolines with 8 to 18 carbon atoms in each of the alkyl or acyl groups, as well as cocoacylaminoethyl hydroxyethyl carboxymethyl glycinate. A preferred zwitterionic surfactant is the fatty acid amide derivative known under the INCI name Cocamidopropyl Betaine.

Ampholytes are include surface-active compounds that apart from a $C_{8-24}$ alkyl or acyl group, comprise at least one free amino group and at least one $—COOH$ or $—SO_3H$ group in the molecule, and are able to form internal salts. Examples of suitable ampholytes are N-alkylglycines, N-alkyl propionic acids, N-alkylamino butyric acids, N-alkylimino dipropionic acids, N-hydroxyethyl-N-alkylamidopropylglycine, N-alkyltaurines, N-alkylsarcosines, 2-alkylamino propionic acids and alkylamino acetic acids, each with about 8 to 24 carbon atoms in the alkyl group. Particularly preferred ampholytes are N-cocoalkylamino propionate, cocoacylaminoethylamino propionate and $C_{12}$-$C_{18}$ acyl sarcosine.

Nonionic surfactants comprise, for example, a polyol group, a polyalkylene glycol ether group, or a combination of polyol ether and polyglycol ether groups as the hydrophilic group. Exemplary compounds of this type are
- addition products of 2 to 50 moles ethylene oxide and/or 1 to 5 moles propylene oxide to linear and branched fatty alcohols containing 8 to 30 carbon atoms, to fatty acids containing 8 to 30 carbon atoms, and to alkyl phenols containing 8 to 15 carbon atoms in the alkyl group,
- methyl or $C_2$-$C_6$ alkyl group end blocked addition products of 2 to 50 moles ethylene oxide and/or 1 to 5 moles propylene oxide to linear and branched fatty alcohols with 8 to 30 carbon atoms, to fatty acids with 8 to 30 carbon atoms and to alkyl phenols with 8 to 15 carbon atoms in the alkyl group, such as the commercially available Dehydrol® LS, Dehydrol® LT (Cognis),
- $C_{12}$-$C_{30}$ fatty acid mono- and diesters of addition products of 1 to 30 moles ethylene oxide to glycerine,
- addition products of 5 to 60 moles ethylene oxide on castor oil and hydrogenated castor oil,
- polyol esters of fatty acids, such as the commercial product Hydagen® HSP (Cognis) or Sovermol types (Cognis),
- alkoxylated triglycerides,
- alkoxylated fatty acid alkyl esters of the formula (E4-I)

$$R^1CO—(OCH_2CHR^2)_w OR^3 \qquad (E4-I)$$

wherein $R^1CO$ is a linear or branched, saturated and/or unsaturated acyl group containing 6 to 22 carbon atoms, $R^2$ is hydrogen or methyl, $R^3$ is linear or branched alkyl groups containing 1 to 4 carbon atoms and x is a number from 1 to 20,
- amine oxides,
- mixed hydroxy ethers, such as described in DE-OS 1 973 8866,
- sorbitol esters of fatty acids and addition products of ethylene oxide to sorbitol esters of fatty acids such as polysorbates,
- sugar esters of fatty acids and addition products of ethylene oxide to sugar esters of fatty acids,
- addition products of ethylene oxide to fatty acid alkanolamides and fatty amines,
- sugar surfactants of the type alkyl and alkenyl oligoglycosides according to Formula (E4-II),

$$R^4O—[G]_p \qquad (E4-II)$$

wherein $R^4$ is an alkyl or alkenyl group containing 4 to 22 carbon atoms, G is a sugar group containing 5 or 6 carbon atoms and p is a number from 1 to 10. They can be obtained according to appropriate methods of preparative organic chemistry.

Alkyl and alkenyl oligoglycosides can be derived from aldoses or ketoses containing 5 or 6 carbon atoms, preferably from glucose. The index value p in the general Formula (E4-II) represents the degree of oligomerization (DP) (i.e., the distribution of mono and oligoglycosides) and is a number between 1 and 10. In a single molecule, p is a whole number and can assume the values 1 to 6. The value p for a specific alkyl oligoglycoside is an analytically determined, calculated quantity that mostly represents a fractional number. Preferably, alkyl and/or alkenyl oligoglycosides are employed having an average degree of oligomerization p of 1.1 to 3.0. Alkyl oligoglucosides with chain lengths $C_8$-$C_{10}$ (DP=1 to 3) are preferred, which result as the low boiling fraction in the separative distillation of industrial $C_8$-$C_{18}$ coco fatty alcohol and which can be contaminated with a fraction of less than 6 wt. % of $C_{1-2}$ alcohol, as well as alkyl oligoglucosides based on industrial $C_{9/11}$ oxo alcohols (DP=1 to 3). The alkyl or alkenyl group $R^{15}$ can moreover be derived from primary alcohols containing 12 to 22, preferably 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as their industrial mixtures that can be obtained as described above. Alkyl oligoglucosides based on hydrogenated $C_{12/14}$ coco alcohol with a DP of 1 to 3 are preferred.

Alkylene oxide addition products to saturated, linear fatty alcohols and fatty acids, each with 2 to 30 moles ethylene oxide per mole fatty alcohol or fatty acid, have proved to be preferred non-ionic surfactants. Preparations with excellent properties are also obtained when they comprise fatty acid esters of ethoxylated glycerine as the non-ionic surfactant.

These compounds are characterized by the following parameters. The alkyl group R comprises 6 to 22 carbon atoms and may be both linear and also branched. Primary linear aliphatic groups and aliphatic groups that are methyl-branched in the 2-position are preferred. Such alkyl groups include 1-octyl, 1-decyl, 1-lauryl, 1-myristyl, 1-cetyl and 1-stearyl. 1-Octyl, 1-decyl, 1-lauryl, 1-myristyl are particularly preferred. On using so-called "oxo alcohols" as starting materials, compounds with an odd number of carbon atoms in the alkyl chain preponderate.

Sugar surfactants can also be used as the non-ionic surfactants. They are preferably included in amounts of about 0.1 to about 20 wt. %, based on total composition. Quantities of about 0.5 to about 15 wt. % are particularly preferred, and quantities of about 0.5 to about 7.5 wt. % are quite particularly preferred.

For compounds with alkyl groups that are used as surfactants, they can be pure substances. However, it is normally preferred to start with natural vegetal or animal raw materials for the manufacture of these materials, with the result that mixtures of substances are obtained having different alkyl chain lengths based on the raw material used.

For surfactants represented by the addition products of ethylene oxide and/or propylene oxide to fatty alcohols or derivatives of these addition products, both products with a "normal" homolog distribution as well as those with a narrow homolog distribution may be used. "Normal" homolog distribution refers to mixtures of homologs obtained from the reaction of fatty alcohols and alkylene oxide using alkali metals, alkali metal hydroxides or alkali metal alcoholates as catalysts. On the other hand, narrow homolog distributions are obtained if, for example, hydrotalcite, alkaline earth metal salts of ether carboxylic acids, alkaline earth metal oxides, hydroxides or alcoholates are used as catalysts. Use of products with a narrow homolog distribution can be preferred.

Additional surfactants are generally added in quantities of about 0.1 to about 45 wt. %, preferably about 0.5 to about 30 wt. % and quite particularly preferably from about 0.5 to about 25 wt. %, based on total composition. The amount added depends upon the type of inventive agent. For a shampoo or other cleansing agent, surfactant levels above about 45 wt. % are typical.

The agents can additionally comprise at least one emulsifier. Emulsifiers act at the interface to produce water or oil-stable adsorption layers that protect the dispersed droplets against coalescence and thereby stabilize the emulsion. Thus, emulsifiers, like surfactants, are composed of hydrophobic and hydrophilic molecular moieties. Hydrophilic emulsifiers preferably form O/W emulsions and hydrophobic emulsifiers preferably form W/O emulsions. The choice of this emulsifying surfactant or emulsifier depends on the materials being dispersed and the respective external phase as well as the fineness of the emulsion. Exemplary emulsifiers usable according to the invention are

- addition products of 4 to 100 moles ethylene oxide and/or 1 to 5 moles propylene oxide to linear fatty alcohols containing 8 to 22 carbon atoms, to fatty acids containing 12 to 22 carbon atoms and to alkyl phenols containing 8 to 15 carbon atoms in the alkyl group,
- $C_{12}$-$C_{22}$ fatty acid mono- and diesters of addition products of 1 to 30 moles ethylene oxide on polyols containing 3 to 6 carbon atoms, especially glycerine,
- ethylene oxide and polyglycerine addition products on methyl glucoside fatty acid esters, fatty acid alkanolamides and fatty acid glucamides,
- $C_8$-$C_{22}$ alkyl mono and oligoglycosides and their ethoxylated analogs, wherein the degrees of oligomerization are 1.1 to 5, particularly 1.2 to 2.0, and glucose as the sugar component is preferred,
- mixtures of alkyl (oligo) glucosides and fatty alcohols, for example, the commercially available product Montanov® 68,
- addition products of 5 to 60 moles ethylene oxide on castor oil and hydrogenated castor oil,
- partial esters of polyols containing 3-6 carbon atoms with saturated fatty acids containing 8 to 22 carbon atoms,
- sterols. Sterols are understood to mean a group of steroids, which carry a hydroxyl group on carbon atom 3 of the steroid skeleton and are isolated from both animal tissue (zoosterols) and vegetal fats (phytosterols). Examples of zoosterols are cholesterol and lanosterol. Examples of suitable phytosterols are ergosterol, stigmasterol and sitosterol. Sterols, the so-called mycosterols, are also isolated from fungi and yeasts.
- Phospholipids. These include glucose-phospholipids, obtained, for example, as lecithins or phosphatidyl cholines from, for example, egg yolk or plant seeds (e.g. soya beans).
- fatty acid esters of sugars and sugar alcohols such as sorbitol,
- polyglycerines and polyglycerine derivatives such as polyglycerine poly-12-hydroxystearate (commercial product Dehymuls® PGPH),
- linear and branched fatty acids containing 8 to 30 carbon atoms and their Na, K, ammonium, Ca, Mg and Zn salts.

Emulsifiers are preferably added in amounts of about 0.1 to about 25 wt. %, especially about 0.1 to about 3 wt. %, based on total composition.

Non-ionic emulsifiers with an HLB value of 8 to 18 are preferred according to the definition listed in Römpp-Lexikon Chemie (Ed. J. Falbe, M. Regitz), 10th edition, Georg Thieme Verlag Stuttgart, New York, (1997), page 1764. Non-ionic emulsifiers with an HLB value of 10 to 16 are particularly preferred according to the invention.

If the inventive agents are hair dyes, then they additionally have at least one oxidation dye precursor and/or at least one substantive dye. Known developer components, optionally combined with at least one coupler component, can be employed as the oxidation dye precursor.

Substantive dyes are usually nitrophenylenediamines, nitroamino phenols, azo dyes, anthraquinones or indophenols. Preferred substantive dyestuffs are the compounds known under the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, FTC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52 as well as 1,4-diamino-2-nitrobenzene, 2-amino-4-nitrophenol, 1,4-bis(β-hydroxyethyl)amino-2-nitrobenzene, 3-nitro-4-(β-hydroxyethyl)aminophenol, 2-(2'-hydroxyethyl)amino-4,6-dinitrophenol, 1-(T-hydroxyethyl)amino-4-methyl-2-nitrobenzene, 1-amino-4-(2'-hydroxyethyl)-amino-5-chloro-2-nitrobenzene, 4-amino-3-nitrophenol, 1-(T-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-1-hydroxy-4-nitrobenzene.

Inventive compositions according to this embodiment comprise substantive dyes preferably in a quantity of about 0.001 to about 20 wt. %, based on total composition.

In addition, compositions according to the invention can also comprise naturally occurring dyestuffs found, for example, in henna red, henna neutral, henna black, camomile leaves, sandalwood, black tea, alder buckthorn bark, sage, logwood, madder root, cachou, cedar and alkanet root.

It is not required that each substantive dyestuff be pure compounds. In fact, compositions according to the invention, due to manufacturing processes for individual dyestuffs, may comprise minor quantities of even more components, in so far as the latter have no detrimental influence on the styling result or must be excluded on other grounds (e.g., toxicological).

In addition to the components mentioned above, the compositions can further include all active substances, additives and auxiliaries known for such cosmetics.

Further exemplary active products, auxiliaries and additives are

- thickeners like agar-agar, guar gum, alginates, xanthane gum, gum arabica, karaya gum, locust bean flour, linseed gums, dextrans, cellulose derivatives (e.g., methyl cellulose, hydroxyalkyl cellulose and carboxymethyl cellulose), starch fractions and derivatives such as amylose, amylopectin and dextrins, clays such as bentonite, synthetic hydrocolloids such as polyvinyl alcohol, and optionally crosslinked polyacrylates, structurants such as maleic acid and lactic acid, perfume oils, dimethyl isosorbitol and cyclodextrins, solvents and solubilizers such as ethanol, isopropanol, ethylene glycol, propylene glycol, glycerine and diethylene glycol, quaternized amines, such as methyl 1-alkylamidoethyl-2-alkylimidazolium methosulfate defoamers such as silicones, dyestuffs to color the composition, anti-dandruff active materials like Piroctone Olamine, Zinc Omadine and Climbazole, substances for adjusting the pH, such as, for example, customary acids, in particular food acids, and bases, cholesterol, thickeners like sugar esters, polyol esters or polyol alkyl ethers, fats and waxes like spermaceti, beeswax, montan wax and paraffins, fatty acid alkanolamides, chelating agents like EDTA, NTA, β-alanine diacetic acid and phosphonic acids, swelling and penetration compositions such as glycerine, propylene glycol monoethyl ether, carbonates, hydrogen carbonates, guanidines, ureas, and primary, secondary and tertiary phosphates, opacifiers such as latex, styrene/PVP copolymers and styrene/acrylamide copolymers, pearlizing compositions such as ethylene glycol mono- and distearate as well as PEG-3-distearate, preservatives, stabilizers for hydrogen peroxide and other oxidizing compositions, propellants such as propane-butane mixtures, $N_2O$, dimethyl ether, $CO_2$ and air, antioxidants.

Concerning further optional ingredients and their amounts used, reference is expressly made to relevant handbooks known to one skilled in the art.

Formulation of the inventive agents can be in all usual cosmetic forms, for example, in the form of solutions applied as skin or hair pump or aerosol spray onto the skin or hair, in the form of creams, emulsions, waxes or gels, or also surfactant-containing foaming solutions or other preparations suitable for application on the skin or the hair.

However, the inventive agents preferably concern agents for temporary shaping of keratin-containing fibers (i.e., styling agents). Preferred styling agents include styling gels, pump hair sprays, aerosol hair sprays, pump hair foams and aerosol hair foams.

Hair foams refer to compositions that form foam when removed from a suitable container. It may be required to add ingredients to the agent which promote foaming or which stabilize an initially formed foam. Surfactants and/or emulsifiers are particularly suitable for this, as has been described previously. Preferably, cationic surfactants are utilized.

Hair creams and hair gels generally comprise structurants and/or thickening polymers which provide the desired consistency to the products. Structurants and/or thickening polymers are typically added in amounts of about 0.1 to about 10 wt. %, based on total product. Quantities of about 0.5 to about 5 wt. %, particularly about 0.5 to about 3 wt. %, are preferred. However, as the inventively added polymer combination possesses self-thickening properties, the addition of additional structurants and/or thickening polymers may not be required. The inventive agents preferably comprise no additional structurants and/or thickening polymers.

When the inventive agents are in the form of an aerosol product, then this imperatively comprises a propellant.

Suitable propellants include $N_2O$, dimethyl ether, $CO_2$, air and alkynes containing 3 to 5 carbon atoms, such as propane, n-butane, iso-butane, n-pentane and iso-pentane, and their mixtures. Dimethyl ether, propane, n-butane, iso-butane and their mixtures are preferred.

The cited alkanes, mixtures of the cited alkanes or mixtures of the cited alkanes with dimethyl ether are preferred as the sole propellant. However, the invention also explicitly includes the joint utilization with propellants of the fluorochlorohydrocarbon type, especially fluorinated hydrocarbons.

The size of aerosol droplets or foam bubbles and the relevant size distribution can be adjusted for a given spray device by adjusting the weight ratio of propellant to the usual ingredients in the formulation.

The quantity of added propellant varies as a function of the actual composition of the agent, packaging used and desired product type (e.g., hair spray or hair foam). When a conventional spray device is used, aerosol foam products preferably comprise propellant in amounts of about 1 to about 35 wt. %, based on total product. Quantities of about 2 to about 30 wt. %, particularly about 3 to about 15 wt. %, are particularly preferred. Aerosol sprays generally comprise greater amounts of propellant. For aerosols, the propellant is preferably added in amounts of about 30 to about 98 wt. %, based on total product. Quantities of about 40 to about 95 wt. %, especially about 50 to about 95 wt. %, are particularly preferred.

Aerosol products can be manufactured according to conventional techniques. Generally, all ingredients of the agent except the propellant are charged into a suitable pressure-resistant container. This is then sealed with a valve. The desired quantity of propellant is then filled by conventional techniques.

Accordingly, a second subject matter of the invention is a process in which the inventive cosmetic agent is applied onto hair in the form of a pump hair spray, aerosol hair spray, pump hair foam, aerosol hair foam or styling gel and is optionally worked into the hair with the palms of the hand and/or the fingers.

The desired shaping of the hair can then be carried out with the fingers or hands as well as with suitable conventional aids such as for example a comb or brush.

A third subject matter of the invention is use of the inventive agent for the temporary shaping of keratin-containing fibers.

The inventive agents and products comprising these agents lend treated hair a very strong and moisture resistant hair set.

EXAMPLES

The following examples are intended to illustrate the subject matter of the present invention in more detail, without limiting it in any way.

Unless otherwise stated, the quantities are understood to be in weight percent.

Example 1

Inventive styling agents A to F were manufactured according to the Table below.

TABLE 1

Styling Agents

| Raw materials | A | B | C | D | E | F |
|---|---|---|---|---|---|---|
| Triethanolamine, 99% | 1.625 | 1.625 | 1.625 | 1.625 | 1.625 | 1.625 |
| Luviflex Soft [1] | 8.335 | 8.335 | 8.335 | 8.335 | 8.335 | 8.335 |
| Diaformer Z 632N [2] | 8.33 | — | — | — | — | — |
| Diaformer Z-651N [3] | — | 8.33 | — | — | — | — |
| Diaformer Z-711N [4] | — | — | 6.25 | — | — | — |
| Diaformer Z-712N [5] | — | — | — | 6.25 | — | — |
| Diaformer Z-712W [6] | — | — | — | — | 11.90 | — |
| Diaformer Z-731N [7] | — | — | — | — | — | 6.25 |
| Water, deionized | ad 100 | ad 100 | ad 100 | ad 100 | ad 100 | ad 100 |

[1] Copolymer of ethyl acrylate and methacrylic acid, 30% dispersion in water (INCI name: Acrylates Copolymer) (BASF)
[2] Copolymer of stearyl acrylate, methacryloyl ethylamine oxide and one or more monomers from acrylic acid, methacrylic acid and their simple esters (28-32 wt. % solids in ethanol; INCI name: Acrylates/Stearyl Acrylate/Ethylamine Oxide Methacrylate Copolymer) (Clariant)
[3] Copolymer of stearyl acrylate, lauryl acrylate, methacryloyl ethylamine oxide and one or more monomers from acrylic acid, methacrylic acid and their simple esters (28-32 wt. % solids in ethanol/water (6:1); INCI name: Acrylates/Stearyl Acrylate/Lauryl Acrylate/Ethylamine Oxide Methacrylate Copolymer) (Clariant)
[4] Copolymer of stearyl acrylate, lauryl acrylate, methacryloyl ethylamine oxide and one or more monomers from acrylic acid, methacrylic acid and their simple esters (38-42 wt. % solids in ethanol/water (5:1); INCI name: Acrylates/Stearyl Acrylate/Lauryl Acrylate/Ethylamine Oxide Methacrylate Copolymer) (Clariant)
[5] Copolymer of stearyl acrylate, lauryl acrylate, methacryloyl ethylamine oxide and one or more monomers from acrylic acid, methacrylic acid and their simple esters (38-42 wt. % solids in ethanol/water (5:1); INCI name: Acrylates/Stearyl Acrylate/Lauryl Acrylate/Ethylamine Oxide Methacrylate Copolymer) (Clariant)
[6] Copolymer of stearyl acrylate, lauryl acrylate, methacryloyl ethylamine oxide and one or more monomers from acrylic acid, methacrylic acid and their simple esters (38-42 wt. % solids in ethanol/water; INCI name: Acrylates/Stearyl Acrylate/Lauryl Acrylate/Ethylamine Oxide Methacrylate Copolymer) (Clariant)
[7] Copolymer of stearyl acrylate, lauryl acrylate, methacryloyl ethylamine oxide and one or more monomers from acrylic acid, methacrylic acid and their simple esters (38-42 wt. % solids in ethanol/water (5:1); INCI name: Acrylates/Stearyl Acrylate/Lauryl Acrylate/Ethylamine Oxide Methacrylate Copolymer) (Clariant)

Strands of hair (Kerling Internationale Haarfabrik GmbH, Art.-Nr. 826500 Klebetresse dicht; 0.9 g) were washed with sodium laurethsulfate (12.5 wt. % in water) and treated with ethanol (50 wt. % in water) at 50° C. The strands were then thoroughly rinsed out with lukewarm water and combed through. Excess water was squeezed out of the strands between the index finger and thumb, and the strands were dried overnight at 45° C.

Application procedures for:

Hair sprays:

The strand was uniformly sprayed for 2 s on each side from a distance of 10 cm.

Styling mousses:

The mousse was applied in the weight ratio 1:2 to the strand weight and spread out onto the strand with the fingers and worked in.

Gel/Cream/Wax:

The gel was applied in the weight ratio 1:2 to the strand weight and spread out onto the strand with the fingers and worked in.

The prepared strand was dried on a plaque at 45° C. for 1 hour and then carefully removed from the plaque with a needle that had previously been placed between the strand and the plaque.

The strands prepared with styling gels A to F, fixed next to one another and parallel by clips to a bar. The bar was rotated such that all the strands were horizontally aligned. The bar was then rotated by 90° and the strands—which were then vertically aligned—were dipped for 5 seconds into a box that was filled with water or salt water (simulating perspiration) maintained at room temperature. The strand was then again rotated back by 90° and the deflection of the strands of hair from the starting value was measured.

All inventive examples provided excellent shape stability after dipping in water and very good shape stability after dipping in salt water (see Table 2).

TABLE 2

Shape stability in the dip test

| Styling gel | Deflection after water[1] | Deflection after salt water[1] |
|---|---|---|
| A | 98% | 92% |
| B | 104% | 96% |
| C | 109% | 93% |
| D | 105% | 93% |
| E | 101% | 86% |
| F | 97% | 87% |

[1] A value of 100% corresponds to zero deflection (i.e., complete shape stability). A value less than 100% corresponds to a corresponding deflection from the horizontal and thereby a loss of shape stability. Deviations of ±5% are within the measurement accuracy.

Example 2

In a comparative experiment, strands of hair pre-treated with the same applied amounts of styling gel according the inventive composition as well as with two commercial styling gels were prepared and dried. A gel based on polyvinyl pyrrolidinone as well as a gel based on vinyl pyrrolidinone/vinyl acetamide/vinylimidazole copolymer were used as the commercial styling gels. The strands prepared in this manner were fixed next to one another and parallel by clips to a bar.

i) A horizontal suspension of the strands did not lead to any buckling of the strands prepared with inventive or commercial agents, thereby demonstrating the equivalence of shape stability of the inventive composition against commercial styling gels.

ii) In an additional step the prepared strands were suspended vertically into a water bath maintained at room temperature. A significant loss of shape stability was observed after 1 minute in the water bath for those strands prepared with the commercial styling gels, whereas the strands prepared with the inventive composition did not exhibit any loss of stability.

iii) After 4 minutes in the water bath, the commercial styling gels were dissolved to such an extent that the prepared strands no longer showed shape stability, whereas the inventively prepared strands still remained shape stable.

iv) After 5 minutes, the strands were removed from the water bath and suspended horizontally again. The strands prepared with the commercial styling gels hung down without hold and shape, whereas the inventively prepared strands of hair still retained their shape stability and remained almost horizontally aligned.

We claim:

1. A cosmetic agent comprising in a cosmetically acceptable carrier:
    a) at least one copolymer A made up from
        at least two monomers A1, wherein the first monomer is chosen from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer is chosen from acrylic acid stearyl ester and methacrylic acid stearyl ester, and
        at least one monomer A2 chosen from (meth)acryloyl alkylamine oxides of Formula A2-II

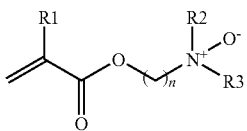

(A2-II)

wherein in Formula A2-II R1 is H or $CH_3$, R2 and R3 are independently an optionally branched $C_1$-$C_{10}$ alkyl, and n is a whole number from 1 to 20, and wherein the copolymer A is selected from Acrylates/Stearyl Acrylate/Ethylamine Oxide Methacrylate Copolymer present in 28 to 32 wt. % of solids in ethanol, and
    b) a methacrylic acid/ethyl acrylate film-forming and/or setting anionic polymer B, and wherein copolymer A and the film forming and/or setting anionic polymer B are present in a weight ratio of about 1:1, and wherein the copolymer A is present in an amount of about 1 to about 12 wt. %, based on total weight of the agent, and the film forming and/or setting anionic polymer B is present in an amount of about 1 to about 10 wt. %, based on total weight of the agent.

2. Method of styling hair comprising applying a cosmetic agent according claim 1 onto the hair by pump hair spray, aerosol hair spray, pump hair foam, aerosol hair foam or styling gel, and optionally working the agent into the hair with the palms of the hand and/or the fingers.

3. A cosmetic agent comprising in a cosmetically acceptable carrier:
    a) at least one copolymer A made up from
        at least two monomers A1, wherein the first monomer is chosen from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester and methacrylic acid isopropyl ester, and the second monomer is chosen from acrylic acid stearyl ester and methacrylic acid stearyl ester, and
        at least one monomer A2 chosen from (meth)acryloyl alkylamine oxides of Formula A2-II

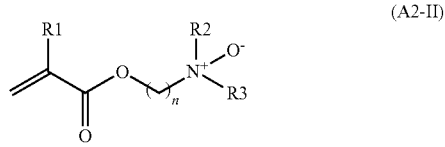

(A2-II)

wherein in Formula A2-II R1 is H or $CH_3$, R2 and R3 are independently an optionally branched $C_1$-$C_{10}$ alkyl, and n is a whole number from 1 to 20, and wherein the copolymer A is selected from Acrylates/Stearyl Acrylate/Ethylamine Oxide Methacrylate Copolymer present in 28 to 32 wt. % of solids in ethanol, and
    b) a methacrylic acid/ethyl acrylate film-forming and/or setting anionic polymer B, wherein copolymer A is present in an amount of about 2.5 wt. %, based on total weight of the agent, and the film forming and/or setting anionic polymer B is present in an amount of about 2.5 wt. %, based on the total weight of the agent, and wherein copolymer A and the film forming and/or setting anionic polymer B are present in a weight ratio of about 1:1.

* * * * *